(12) United States Patent
Wu et al.

(10) Patent No.: US 11,376,271 B1
(45) Date of Patent: Jul. 5, 2022

(54) METHODS OF AMELIORATING THE EFFECTS OF ALCOHOLIC LIVER DAMAGE

(71) Applicants: FULGENT LIFE INC., Irvine, CA (US); GUANG DONG HAO BANG YI YAO JIAN KANG CO., LTD., Guang Dong (CN)

(72) Inventors: Yong Wu, Los Angeles, CA (US); Fei Zhou, Irvine, CA (US); Shengzhen Tang, La Verne, CA (US); Ke Wu, Downey, CA (US); Shiliu Tian, Downey, CA (US); Long Yi, GuangDong (CN)

(73) Assignees: FULGENT LIFE INC., Irvine, CA (US); GUANGDONG HAIHE BIOMEDICAL TECHNOLOGY CO., LTD., Guang Dong (CN)

( * ) Notice: Subject to any disclaimer, the term of this patent is extended or adjusted under 35 U.S.C. 154(b) by 0 days.

(21) Appl. No.: 17/221,734

(22) Filed: Apr. 2, 2021

(51) Int. Cl.
*A61K 31/7084* (2006.01)
*A23L 33/13* (2016.01)
*A61P 1/16* (2006.01)

(52) U.S. Cl.
CPC .......... *A61K 31/7084* (2013.01); *A23L 33/13* (2016.08); *A61P 1/16* (2018.01)

(58) Field of Classification Search
CPC ........ A61K 31/7084; A23L 33/13; A61P 1/16
See application file for complete search history.

(56) References Cited

U.S. PATENT DOCUMENTS

| 5,053,396 | A | 10/1991 | Blass | |
|---|---|---|---|---|
| 2005/0271739 | A1 | 12/2005 | Wang | |
| 2019/0076456 | A1* | 3/2019 | McNerlin | ............ A61K 9/0078 |

FOREIGN PATENT DOCUMENTS

| CN | 105535945 | A | | 5/2016 | |
|---|---|---|---|---|---|
| CN | 109602756 | A | * | 4/2019 | ......... A61K 31/7024 |

OTHER PUBLICATIONS

Definition of prevent, Oxford English Dictionary Online, http://dictionary.oed.com/, accessed online Mar. 27, 2010, especially definition 9a. at p. 2. (Year: 2010).*
Bruha et al., World J. Hepatol., 2012, 4(3), p. 81-90. (Year: 2012).*
Pittler et al., BMJ, 2005, 331:1515, 4 pgs. (Year: 2005).*
International Search Report and Written Opinion for International Application No. PCT/US21/25672, dated Jun. 30, 2021, 8 pages.
Agarwal S, Fulgoni VL, 3rd, Lieberman HR: Assessing alcohol intake & its dose-dependent effects on liver enzymes by 24-h recall and questionnaire using NHANES 2001-2010 data. *Nutr J* 2016, 15(1):62.
European Association for the Study of L: EASL clinical practical guidelines: management of alcoholic liver disease. *J Hepatol* 2012, 57(2):399-420.
Fattovich G, Stroffolini T, Zagni I, Donato F: Hepatocellular carcinoma in cirrhosis: incidence and risk factors. *Gastroenterology* 2004, 127(5 Suppl 1):S35-50.
Goldberg DM, Watts C: Serum enzyme changes as evidence of liver reaction to oral alcohol. *Gastroenterology* 1965, 49(3):256-261.
Isse T, Matsuno K, Oyama T, Kitagawa K, Kawamoto T, "Aldehyde dehydrogenase 2 gene targeting mouse lacking enzyme activity shows high acetaldehyde level in blood, brain, and liver after ethanol gavages," *Alcohol Clin Exp Res* 2005, 29(11): 1959-1964.
Lee HS, Isse T, Kawamoto T, Woo HS, Kim AK, Park JY, Yang M, "Effects and action mechanisms of Korean pear (*Pyrus pyrifolia cv. Shingo*) on alcohol detoxification," *Phytother Res* 2012, 26(11): 1753-1758.
Li W, Sauve AA, "NAD(+) content and its role in mitochondria," *Methods Mol Biol* 2015, 1241:39-48.
Marra F, Efsen E, Romanelli RG, Caligiuri A, Pastacaldi S, Batignani G, Bonacchi A, Caporale R, Laffi G, Pinzani M et al: Ligands of peroxisome proliferator-activated receptor gamma modulate profibrogenic and proinflammatory actions in hepatic stellate cells. *Gastroenterology* 2000, 119(2):466-478.
Morgan TR, Mandayam S, Jamal MM: Alcohol and hepatocellular carcinoma. *Gastroenterology* 2004, 127(5 Suppl 1):S87-96.
Ozburn AR, Harris RA, Blednov YA, "Chronic voluntary alcohol consumption results in tolerance to sedative/hypnotic and hypothermic effects of alcohol in hybrid mice," *Pharmacol Biochem Behav* 2013, 104:33-39.
Preiss J, Handler P: Biosynthesis of diphosphopyridine nucleotide. I. Identification of intermediates. *J Biol Chem* 1958, 233(2):488-492.
Preiss J, Handler P: Biosynthesis of diphosphopyridine nucleotide. II. Enzymatic aspects. *J Biol Chem* 1958, 233(2):493-500.
Remington's Pharmaceutical Sciences, Mack Publishing Company, Easton, Pa., 18th edition, 1990.
Siegmund S, Haas S, Schneider A, Singer MV: Animal models in gastrointestinal alcohol research-a short appraisal of the different models and their results. *Best Pract Res Clin Gastroenterol* 2003, 17(4):519-542.
Sonavane M, Hayat F, Makarov M, Migaud ME, Gassman NR: Dihydronicotinamide riboside promotes cell-specific cytotoxicity by tipping the balance between metabolic regulation and oxidative stress. *PLoS One* 2020, 15(11):e0242174.
Westphal JF, Brogard JM: Drug administration in chronic liver disease. *Drug Saf* 1997, 17(1):47-73.
Yang T, Sauve AA: NAD metabolism and sirtuins: metabolic regulation of protein deacetylation in stress and toxicity. *AAPS J* 2006, 8(4):E632-643.

(Continued)

*Primary Examiner* — Jonathan S Lau
(74) *Attorney, Agent, or Firm* — Lewis Roca Rothgerber Christie LLP

(57) ABSTRACT

According to embodiments of the present disclosure, a method of treating, preventing or ameliorating acute alcoholic liver damage in a subject comprises administering to the subject an exogenous source of nicotinamide adenine dinucleotide (NAD+) comprising NADH (nicotinamide adenine dinucleotide (NAD)+hydrogen (H)) or NRH (dihydronicotinamide nucleoside). Administration of the exogenous source of NAD+ may also be used to increase a subject's tolerance to alcohol, and/or to treat, prevent or alleviate the symptoms of an alcohol hangover.

19 Claims, 12 Drawing Sheets
(12 of 12 Drawing Sheet(s) Filed in Color)

(56) References Cited

OTHER PUBLICATIONS

Yang H, Yang T, Baur JA, Perez E, Matsui T, Carmona JJ, Lamming DW, Souza-Pinto NC, Bohr VA, Rosenzweig A et al: Nutrient-sensitive mitochondrial NAD+ levels dictate cell survival. *Cell* 2007, 130(6): 1095-1107.
Yang Y, Mohammed FS, Zhang N, Sauve AA: Dihydronicotinamide riboside is a potent NAD(+) concentration enhancer in vitro and in vivo. *J Biol Chem* 2019, 294(23):9295-9307.

* cited by examiner

METHODS OF AMELIORATING THE EFFECTS OF ALCOHOLIC LIVER DAMAGE

BACKGROUND

Alcohol is a psychoactive substance that has been consumed by several cultures for many centuries. However, alcohol is also an addictive substance that can lead to abuse or alcoholism. Alcoholism, in turn, leads to many diseases, and if the alcohol abuse continues unchecked, it can lead to death.

For example, alcohol consumption is a main cause of acute liver injury and chronic liver disease. One such disease includes Alcoholic Liver Disease (ALD), which is characterized by liver fat accumulation at first, but which can lead to end-stage liver failure after an inflammatory response. Indeed, alcoholism can accelerate many types of liver diseases, including Alcoholic Fatty Liver Disease (AFLD), alcoholic steatohepatitis, Alcoholic Hepatitis (AH), progressive fibrosis, liver cirrhosis and liver failure. Patients with ALD, especially those that have progressed to alcoholic cirrhosis, have an augmented risk of developing Hepatocellular Carcinoma (HCC). As such, alcoholism is a social and economic burden on many societies. However, to date, there is a dearth of effective treatments for the liver damage caused by heavy or excessive alcohol consumption.

SUMMARY

According to embodiments of the present disclosure, a method of treating, preventing or ameliorating acute alcoholic liver damage in a subject comprises administering to the subject an exogenous source of nicotinamide adenine dinucleotide (NAD+) comprising NADH (nicotinamide adenine dinucleotide (NAD)+hydrogen (H)) and/or NRH (dihydronicotinamide nucleoside). In some embodiments, administration of the exogenous source of NAD+ comprises administering the exogenous source of NAD+ prior to the subject consuming or being exposed to alcohol. In some embodiments, administration of the exogenous source of NAD+ comprises administering the exogenous source of NAD+ after the subject has consumed or been exposed to alcohol.

According to some embodiments, administration of the exogenous source of NAD+ comprises orally administering to the subject a dietary supplement comprising the exogenous source of NAD+. And in some embodiments, administration of the exogenous source of NAD+ comprises orally administering to the subject a pharmaceutical composition comprising the exogenous source of NAD+. The pharmaceutical composition may further comprise one or more pharmaceutically acceptable carriers, excipients, adjuvants and/or diluents.

In some embodiments, administration of the exogenous source of NAD+ comprises administering a dose of the exogenous source of NAD+ of about 0.01 mg/kg to about 1000 mg/kg per day. Administration of the exogenous source of NAD+ may comprise administering a daily dose of the exogenous source of NAD+. And in some embodiments, administration of the exogenous source of NAD+ may comprise administering a daily dose of the exogenous source of NAD+ for a period of 1 day to 14 days.

According to some embodiments of the present disclosure, a method of increasing a subject's tolerance of alcohol comprises administering to the subject an exogenous source of nicotinamide adenine dinucleotide (NAD+) comprising NADH (nicotinamide adenine dinucleotide (NAD)+hydrogen (H)) and/or NRH (dihydronicotinamide nucleoside). Administration of the exogenous source of NAD+ may comprise administering the exogenous source of NAD+ prior to the subject consuming or being exposed to alcohol. In some embodiments, administration of the exogenous source of NAD+ comprises orally administering to the subject a dietary supplement comprising the exogenous source of NAD+. Administration of the exogenous source of NAD+ may comprise administering a dose of the exogenous source of NAD+ of about 0.01 mg/kg to about 1000 mg/kg per day. And administration of the exogenous source of NAD+ may comprise administering a daily dose of the exogenous source of NAD+.

In some embodiments of the present disclosure, a method of treating, preventing or alleviating the symptoms of an alcohol hangover in a subject comprises administering to the subject an exogenous source of nicotinamide adenine dinucleotide (NAD+) comprising NADH (nicotinamide adenine dinucleotide (NAD)+hydrogen (H)) and/or NRH (dihydronicotinamide nucleoside). Administration of the exogenous source of NAD+ may comprise administering the exogenous source of NAD+ prior to the subject consuming or being exposed to alcohol. And in some embodiments, administration of the exogenous source of NAD+ may comprise administering the exogenous source of NAD+ after the subject has consumed or been exposed to alcohol. Administration of the exogenous source of NAD+ may comprise orally administering to the subject a dietary supplement comprising the exogenous source of NAD+. And administration of the exogenous source of NAD+ may comprise administering a dose of the exogenous source of NAD+ of about 0.01 mg/kg to about 1000 mg/kg per day.

BRIEF DESCRIPTION OF THE DRAWINGS

The patent or application file contains at least one drawing executed in color. Copies of this patent or application publication with color drawing(s) will be provided by the Office upon request and payment of the necessary fee.

These and other features and advantages of embodiments of the present disclosure may be better understood by reference to the following detailed description when considered in conjunction with the accompanying drawings, in which.

DETAILED DESCRIPTION

Figure 1:
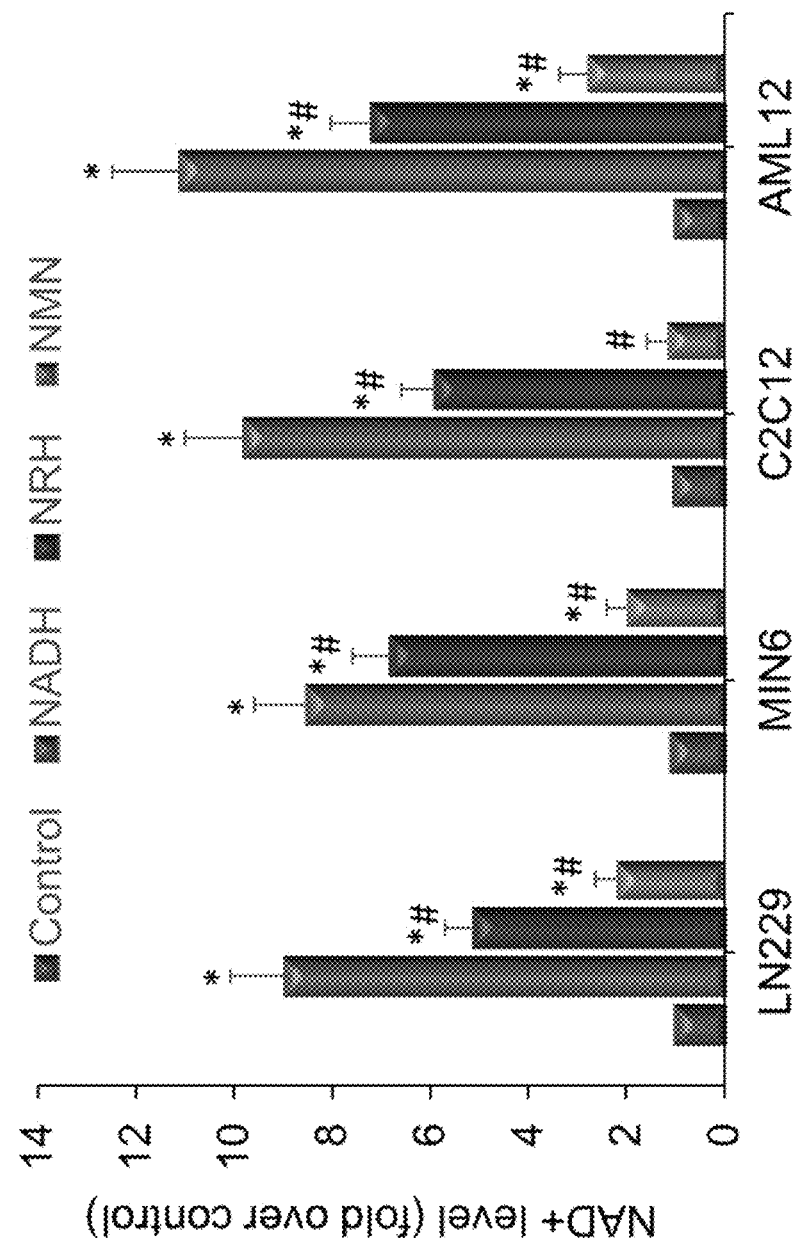
FIG. 1 is a graph comparing the NAD+ levels in various mammalian cell lines (i.e., LN229, MING, and C2C12 and AML12 cells) treated with a control (blue), 1 mM NADH (brown), 1 mM NRH (red), or 1 mM NMN (purple) for 3 h.

Although the biological mechanism of ALD caused by long-term alcohol consumption has been determined, there is no generally accepted treatment to prevent or reverse the damage caused by this disease. And at present, ALD is a leading cause of the increase in morbidity and mortality from alcohol consumption, as well as increases in related medical expenses. As such, the lack of an effective and accepted treatment for the prevention or reversal of liver damage caused by alcoholism is a major drawback of current protocols.

Abstinence from alcohol may restore early damage caused by ALD to a relatively normal state, but as ALD progresses to later stages, conventional wisdom dictates that the damage can become irreversible. This is due, in part, to the fact that long-term alcohol consumption and its consequent damage to the liver involve various changes in the cells and molecules of the liver, which changes may damage the function and metabolism of the liver. This damage to the function and metabolism of the liver complicates treatment protocols because many drugs rely mainly on the liver for metabolism and clearance. However, when the liver is in such a damaged state, these drugs must be used with caution because the liver function damage can reduce drug excretion and increase plasma concentrations of the drug. Consequently, traditional drugs used to treat ALD have limited efficacy, and many patients experience adverse side effects of these drugs.

According to embodiments of the present disclosure, increasing a patient's (or subject's) NAD+ (i.e., nicotinamide adenine dinucleotide) concentration is a natural, harmless and efficient way to prevent or treat liver function damage, ameliorate the effects of liver damage, and/or otherwise improve liver function or protect the liver from sustaining liver damage (or additional liver damage). Additionally, increasing the patient's (or subject's) NAD+ concentration can increase the subject's tolerance for alcohol, and may treat, prevent or alleviate the symptoms of an alcohol hangover.

Nicotinamide adenine dinucleotide (NAD+) is a necessary compound for cell respiration and a key coenzyme existing in all living cells. NAD+ plays the role of electron carrier in oxidation and reduction biochemical reactions in metabolism. The role of NAD+ in cell respiration is well known. When glucose and fatty acids are oxidized, NAD+ can accept a hydride equivalent, which leads to its reduction to NADH. NADH may provide a hydride equivalent, resulting in oxidation back to NAD+. These reduction-oxidation cycles use NAD+ to temporarily store hydride ions, but they do not consume NAD+.

Another major function of NAD+ is to participate in alcohol metabolism. Enzymes related to alcohol metabolism, such as alcohol dehydrogenase (ADH) and aldehyde dehydrogenase (ALDH), utilize NAD+ to drive the chain reaction of alcohol oxidation metabolism. Therefore, NAD+ plays an important role in the metabolism and detoxification of alcohol, as shown in Reaction Scheme 1 below.

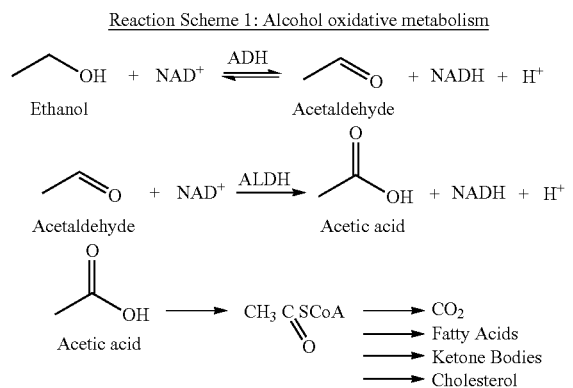

Reaction Scheme 1: Alcohol oxidative metabolism

As shown in Reaction Scheme 1, the first step of alcohol metabolism is catalyzed by ADH, which mainly exists in the liver, and contains a series of isomers. NAD+ needs to accept the reducing equivalents (hydrogen atoms and electrons) from the alcohol. As a result, ethanol is oxidized to acetaldehyde and vitamin cofactor, and NAD+ is reduced to NADH and H+. This ADH reaction is reversible.

The second step is catalyzed by ALDH. Acetaldehyde is oxidized to acetate, and NAD+ is a cofactor which is reduced to NADH. This ALDH reaction is basically irreversible. Most of the acetaldehyde produced by alcohol oxidation is oxidized into acetate in the liver. Under normal circumstances, the circulating level of acetaldehyde is very low.

In the third step, most of the acetate produced by acetaldehyde oxidation leaves the liver and circulates to the surrounding tissues, where it is activated as a key Acetyl CoA. The carbon atoms from alcohol are ultimately the same as the products produced by the oxidation of carbohydrates, fats and proteins, including carbon dioxide, fatty acids, ketone bodies and cholesterol, and which products are formed depends on energy status and nutritional and hormonal conditions.

As discussed generally above, according to embodiments of the present disclosure, alcoholic liver damage can be prevented, treated or ameliorated by increasing a patient's NAD+ concentration. In some embodiments, for example, the patient's NAD+ concentration can be increased by administering to the patient an exogenous source of NAD+. In some embodiments, the exogenous source of NAD+ may be or include NADH (i.e., nicotinamide adenine dinucleotide (NAD)+hydrogen (H)) or NRH (i.e., dihydronicotinamide nucleoside). Additionally, administration of the exogenous source of NAD+ (e.g., NADH or NRH) can increase the subject's tolerance for alcohol, and may treat, prevent or alleviate the symptoms of an alcohol hangover, as discuss further herein.

NADH is a coenzyme existing in all living cells, and includes two nucleotides connected by 5'-phosphate groups, one of which contains an adenine base and the other of which contains nicotinamide. NADH also exists widely in nature and participates in many enzymatic reactions, in which it is alternately oxidized (NAD+) and reduced (NADH) as an electron carrier. NRH is one of the precursors of NAD+ and is a starting point for a novel biosynthetic pathway to NAD+. Administration of NADH or NRH (as the exogenous source of NAD+) surprisingly increases the NAD+ levels in cultured cells significantly more effectively than, for example, supplementation with nicotinamide riboside (NR), nicotinamide mononucleotide (NMN) or vitamin B3 (i.e., nicotinamide combined with niacin). The chemical structures of NADH and NRH are shown below.

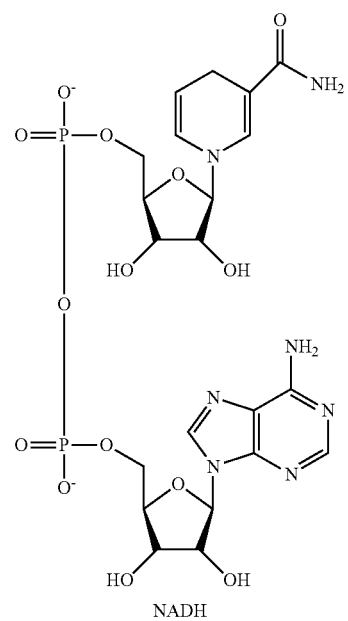

NADH

-continued

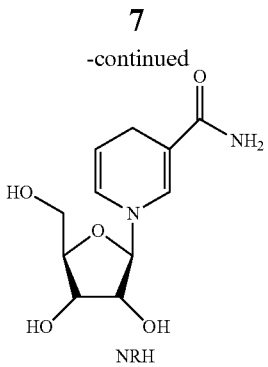

NRH

Timing for the administration of the exogenous source of NAD+ is not particularly limited, and the exogenous source of NAD+ may be administered to a patient (or subject) at any time relative to the alcoholic liver damage or onset of symptoms intended to be treated, prevented or alleviated. For example, in some embodiments, the exogenous source of NAD+ may be administered prior to the consumption of, or exposure to alcohol. In such embodiments, and as disclosed in further detail below, the administration of the exogenous source of NAD+ can protect the liver from alcoholic liver damage that may occur from the subsequent intake of alcohol. Such a pre-treatment with the exogenous source of NAD+ can also increase the subject's tolerance for alcohol, and can prevent the onset of, or reduce the severity or longevity of symptoms associated with an alcoholic hangover (i.e., the adverse physiological side effects associated with the over-consumption of alcohol).

In some embodiments, however, the exogenous source of NAD+ may be administered after the consumption of, or exposure to alcohol. In such embodiments, and as also disclosed in further detail below, the administration of the exogenous source of NAD+ can aid the liver to more quickly and effectively recover from alcoholic liver damage from the intake of alcohol. Such a post-treatment with the exogenous source of NAD+ can also increase the subject's rate of ethanol metabolism, reduce hepatotoxicity due to the alcohol intake, and reduce the severity or longevity of symptoms associated with an alcoholic hangover.

The exogenous source of NAD+ (e.g., the NADH or NRH) may be administered in any suitable manner, without limitation. For example, the exogenous source of NAD+ (e.g., the NADH or NRH) may be administered by parenteral, oral, sublingual, transdermal, topical, intranasal, intratracheal, or intrarectal administration. In certain embodiments, however, the exogenous source of NAD+ (e.g., the NADH or NRH) is administered orally. Such oral administration is not particularly limited, and may be accomplished via a dietary supplement containing the exogenous source of NAD+ (e.g., the NADH or NRH), or via a pharmaceutical composition following a regimen prescribed by a physician. The dietary supplement and/or pharmaceutical composition may be in solid or liquid form, and the solid form may include a tablet, capsule or powder (which powder may be administered in dry form, or may be dispersed or suspended in a liquid).

In some embodiments, the dietary supplement and/or pharmaceutical composition may include the exogenous source of NAD+ (e.g., the NADH or NRH) (or pharmaceutically acceptable salts or derivatives thereof) in a therapeutically or prophylactically effective amount. In some embodiments, the dietary supplements and/or pharmaceutical compositions may include the exogenous source of NAD+ (e.g., the NADH or NRH) (or pharmaceutically acceptable salts or derivatives thereof), as well as one or more pharmaceutically acceptable carriers, excipients, adjuvants or diluents. Acceptable carriers, excipients and diluents are well known in the art and can be selected with regard to the intended route of administration and standard practice. Some non-limiting examples include binders, lubricants, suspending agents, coating agents, solubilizing agents, preserving agents, wetting agents, emulsifiers, surfactants, sweeteners, colorants, flavoring agents, odorants, buffers, antioxidants, stabilizing agents and/or salts.

In some embodiments, for example, the dietary supplements and/or pharmaceutical compositions include at least one pharmaceutically acceptable carrier. The characteristics of the carrier will depend on the route of administration. As used herein, the term "pharmaceutically acceptable" means a non-toxic material that is compatible with a biological system such as a cell, cell culture, tissue, or organism, and that does not interfere with the effectiveness of the biological activity of the active ingredient(s). Thus, dietary supplements and/or pharmaceutical compositions according to embodiments of the present disclosure may contain, in addition to the exogenous source of NAD+ (e.g., the NADH or NRH) (or pharmaceutically acceptable salts or derivatives thereof), one or more diluents, fillers, salts, buffers, stabilizers, solubilizers, and/or other materials well known in the art. The preparation of pharmaceutically acceptable formulations is described in, e.g., Remington's Pharmaceutical Sciences, Mack Publishing Company, Easton, Pa., 18th edition, 1990.

As used herein, the term "pharmaceutically acceptable salt" refers to salts that retain the desired biological activity of the exogenous source of NAD+ (e.g., the NADH or NRH) (or pharmaceutically acceptable salts or derivatives thereof) and exhibit minimal or no undesired toxicological effects. Non-limiting examples of suitable such pharmaceutically acceptable salts include acid addition salts formed with inorganic acids (for example, hydrochloric acid, hydrobromic acid, sulfuric acid, phosphoric acid, nitric acid, and the like), and salts formed with organic acids (such as, e.g., acetic acid, oxalic acid, tartaric acid, succinic acid, malic acid, ascorbic acid, benzoic acid, tannic acid, pamoic acid, alginic acid, polyglutamic acid, naphthalenesulfonic acid, naphthalene disulfonic acid, and polygalacturonic acid).

The exogenous sources of $NAD^+$ (e.g., the NADH or NRH) (or pharmaceutically acceptable salts or derivatives thereof) described herein may also be administered as pharmaceutically acceptable quaternary salts known to those skilled in the art, e.g., quaternary ammonium salts represented by $—N(R)_2—$, wherein R is hydrogen, alkyl, or benzyl, and Z is a counterion (non-limiting examples of which include chloride, bromide, iodide, O-alkyl, toluenesulfonate, methylsulfonate, sulfonate, phosphate, or carboxylate (non-limiting examples of which include benzoate, succinate, acetate, glycolate, maleate, malate, citrate, tartrate, ascorbate, benzoate, cinnamoate, mandeloate, benzyloate, and diphenylacetate).

According to some embodiments, the exogenous source (s) of NAD+ (e.g., the NADH or NRH) (or pharmaceutically acceptable salts or derivatives thereof) described herein may be present in the dietary supplement or pharmaceutical composition together with the pharmaceutically acceptable carrier or diluent in any suitable amount. For example, the exogenous source of NAD+ (e.g., the NADH or NRH) (or pharmaceutically acceptable salts or derivatives thereof) may be present in an amount sufficient to deliver a therapeutically or prophylactically effective amount of the exogenous source of NAD+ (e.g., the NADH or NRH) (or pharmaceutically acceptable salts or derivatives thereof) to a patient or subject without causing (or minimizing the risk of) serious toxic effects in the patient or subject. In some embodiments, for example, the active compound (i.e., exogenous source of NAD+ (e.g., the NADH or NRH) (or pharmaceutically acceptable salts or derivatives thereof)) may be administered by any route in a dose of about 0.01 to 20 mg/kg per day or per dose, for example about 0.01 to 10 mg/kg per day or per dose, or about 5 to about 10 mg/kg per day or per dose. In some embodiments, for example, the active compound may be administered in a dose of about 5 mg/kg per day (or per administration) to about 8 mg/kg per day (or per administration). Additionally, while both NADH and NRH can be administered in similar doses, in some embodiments, the NADH may be administered by any route in a dose of about 5 to about 8 mg/kg per day (or per administration), and the NRH may be administered by any route in a dose of about 5 mg/kg per day (or per administration). As would be understood by those of ordinary skill in the art, the effective dosage range of pharmaceutically acceptable derivatives or salts can be calculated based on the weight of the parent compound to be delivered. And if the derivative or salt exhibits activity in itself, the effective dosage can be estimated as above using the weight of the derivative, or by any other means known to those of ordinary skill in the art. As would be understood by those of ordinary skill in the art, the concentration, treatment or dietary supplement protocol, and administration route will vary depending on the particular patient and extent of liver injury to be treated (or prevented or ameliorated).

Additionally, the dosage regimen for the administration of the exogenous source of NAD+ is not particularly limited, and may be determined on a case-by-case basis by the patient (or subject) or by a prescribing physician. However, it is understood that the dosage regimen may vary depending on the physiology of the subject (or patient), the desired outcome of the regimen (e.g., protection against possible future alcoholic liver damage, or ameliorating the effects of current alcoholic liver damage). In some embodiments, for example, a patient (or subject) administering the exogenous source of NAD+ as a dietary supplement (e.g., prior to consumption of alcohol to protect against possible future alcoholic liver damage) may take a daily dose of the exogenous source of NAD+ indefinitely. In some embodiments, for example, a patient (or subject) administering the exogenous source of NAD+ after consumption of alcohol (e.g., to ameliorate or treat the effects of current alcoholic liver damage) may take a daily dose of the exogenous source of NAD+ for a period time after alcohol consumption sufficient or effective to ameliorate or treat the effects of the alcoholic liver damage. For example, in some embodiments, this patient (or subject) may take a daily dose for 1 day to 14 days, for 3 days to 14 days, or for 3 days to 10 days.

According to embodiments of the present disclosure, administration of the exogenous source of NAD+ can promote alcohol metabolism and prevent or ameliorate early liver injury caused by acute alcohol exposure. As such, administration of the exogenous source of NAD+ (via, for example, a dietary supplement) can prevent or alleviate the harmful effects of excessive drinking. Alternatively or additionally, administration of the exogenous source of NAD+ (via, for example, a pharmaceutical composition) can enhance NAD+ concentration in cells and tissues, thereby protecting and recovering liver function damage caused by alcohol and other detrimental factors.

Indeed, according to embodiments of the present disclosure, increasing a patient's NAD+ concentration via administration of the disclosed dietary supplement and/or pharmaceutical composition treats, prevents, or ameliorates the effects of acute alcoholic liver injury. Specifically, for example, administration of the exogenous source of NAD+ can modify the liver redox fraction (i.e., NAD+/NADH) in a physiological manner, which allows the dehydrogenase reaction to work further towards the ethanol oxidation direction.

Without being bound by any particular theory, it is believed that administering the exogenous source of NAD+ (e.g., via the dietary supplements and/or pharmaceutical compositions according to embodiments of the present disclosure) to a patient accelerates the patient's alcohol metabolism and prevents (or reduces) alcoholic liver injury caused by excessive or heavy alcohol consumption. This acceleration is believed to occur whether the exogenous source of NAD+ is administered before or after alcohol consumption. Again without being bound by any particular theory, it is also believed that administration of the exogenous source of NAD+ according to embodiments of the present disclosure either before or after alcohol consumption significantly reduces increases in plasma levels of aspartate aminotransferase (AST) and alanine transaminase (ALT) normally observed after alcohol consumption, and the administration is therefore therapeutically or prophylactically effective in treating, preventing or reducing alcoholic hepatotoxicity. Also without being bound by any particular theory, it is believed that administration of the exogenous source of NAD$^+$ according to embodiments of the present disclosure also alleviates the abnormal lipid metabolism typically observed in patients with acute alcoholic liver damage. As such, the administration of the exogenous source of NAD+ according to embodiments of the present disclosure can be used to relieve the symptoms of a "hangover" and/or to prevent or treat liver function damage (e.g., acute liver function damage) occurring as a result of excessive or heavy alcohol consumption.

Indeed, according to some embodiments, administration of the exogenous source of NAD+ can improve overall liver health in patients suffering from or at risk of developing acute alcoholic liver damage. For example, as discussed above, in some embodiments, administration of the exogenous source of NAD+ can promote alcohol metabolism and prevent or ameliorate early liver injury caused by acute alcohol exposure. As a result, administration of the exogenous source of NAD+ can eliminate hangovers, or treat, prevent and/or alleviate the symptoms of hangovers. And in some embodiments, administration of the exogenous source of NAD+ can also or alternatively increase the rate of degradation of ethanol and methanol, and increase the patient's metabolization of ethanol, thereby increasing the patient's (or subject's) tolerance of alcohol. Further, in some embodiments, administration of the exogenous source of NAD+ can also or alternatively improve and restore liver function, for example, by activating liver cells. Additionally, in some embodiments, administration of the exogenous source of NAD+ can also or alternatively treat or ameliorate the effects of alcoholic liver damage, including the damage from alcoholic liver disease. Moreover, in some embodiments, administration of the exogenous source of NAD+ can also or alternatively reduce plasma levels of aspartate aminotransferase (AST) and alanine transaminase (ALT). In some embodiments, administration of the exogenous source of NAD+ can also or alternatively reduce levels of low-density lipoproteins and triglycerides. Consequently, administration of the exogenous source of NAD+ can protect the liver, and aid the liver in recovering from liver function damage caused by alcohol and other detrimental factors.

In addition to the liver benefits of administering the exogenous source of NAD+, administration of the exogenous source of NAD+ according to embodiments of the present disclosure can also improve central nervous system health and performance after alcohol intake. For example, without being bound by any particular theory, it is believed that administration of the exogenous source of NAD+ can improve cognitive function after drinking alcohol, and activate nerve cells and brain cells. Indeed, the below experiments demonstrate this cognitive improvement, showing significant reductions in the onset, duration and latency of the loss of righting reflex often experienced after alcohol intake. These cognitive improvements can be had when the exogenous source of NAD+ is administered via any route and at the doses and dosage regimes described herein in connection with the treatment, prevention and/or amelioration of alcoholic liver damage.

Experimental

The following examples and experiments are presented for illustrative purposes only, and do not limit the scope of the present disclosure.

In the following experiments, male C57BL/6J mice were orally fed with alcohol (52% w/v), NADH or NRH. The concentrations of ethanol and acetaldehyde in blood as well as the loss of righting reflex (LORR) were evaluated to indicate alcohol metabolism. The plasma levels of aspartate aminotransferase (AST) and alanine transaminase (ALT) and the levels of malonaldehyde (MDA) and superoxide dismutase (SOD) in liver tissues were tested to reflect the alcohol-induced liver injury. As shown in the below experiments, treatment with NADH or NRH can accelerate alcohol metabolism and prevent alcoholic liver injury caused by excessive drinking, as well as improve cognitive function after alcohol intake. Notably, both pre-treatment and post-treatment with NADH or NRH can significantly reduce increases of AST and ALT after alcohol consumption, indicating that NADH and NRH have therapeutic effects on alcoholic hepatotoxicity, and also prevent (or have prophylactic effects on) the adverse effects of alcohol consumption, including cognitive impairment. Additionally, augmented histological damage, higher hepatic triglyceride (TG) contents and the activity of serum Very Low Density Lipoprotein (VLDL) in acute alcoholic-diet fed mice were also diminished by supplementing with NADH or NRH, suggesting that NADH or NRH can alleviate the abnormal lipid metabolism in acute alcoholic liver damage.

NADH and NRH are also demonstrated to be effective NAD+ concentration-enhancing agents. Compared with NMN, NADH and NRH provided at the same concentration provide greater NAD+ increases. Intraperitoneal injection of NADH and NRH in C57BL/6J mice also significantly increased the NAD+ content in the liver, blood, brain and fat. Importantly, NADH and NRH significantly increased the liver NAD+/NADH ratio, but did not induce apoptosis markers in cells. NADH- or NRH-treated cells are resistant to cell death caused by NAD+-depleting genotoxins, e.g. hydrogen peroxide. Therefore, administration of NADH or NRH to mice can modify the liver redox fraction, NAD+/NADH, in a physiological manner, allowing the dehydrogenase reaction to work further towards the ethanol oxidation direction.

In the following experiments, the vehicle used was phosphate-buffered saline (PBS), unless otherwise indicated.

Also, cells were cultured as follows. LN229, Neuro2a, and C2C12 cells were grown in Dulbecco's modified Eagle's medium (DMEM) supplemented with 10% fetal bovine serum (FBS), 100 units/ml penicillin, and 100 µg/ml streptomycin. MIN6 cells were cultured in DMEM with 15% fetal bovine serum, 100 units/ml penicillin, and 100 µg/ml streptomycin. AML12 cells were cultured in a 1:1 mixture of DMEM high glucose/Ham's F-12 with I-glutamine and supplemented with 10% FCS, 15 mM HEPES, 40 ng/ml dexamethasone, 0.005 mg/ml human recombinant insulin, 5 ng/ml sodium selenite and 0.005 mg/ml transferrin (Sigma Aldrich). Cells were maintained in a humidified incubator supplied with 5% $CO_2$, 95% air at 37° C.

Also, in the below assays, differences between the treatment group and the control group were analyzed by independent t test using the SPSS 20.0 statistical software. All results were expressed as means±SD, as noted in the below discussions. Differences of $p<0.05$ were considered statistically significant.

Elevated NAD+ Concentration Caused by NADH and NRH Exposure

In order to evaluate whether NADH can be absorbed by cells and change NAD+ concentration, some mammalian cell lines (such as insulinogenic (MING), neuronlike (LN229), muscle-like (C2C12), and normal hepatocyte (AML12) cells) were treated with vehicle (control), 1 mM NADH, 1 mM NRH, or 1 mM NMN for 3 h.

The cells were seeded in 6-well plates until they reached approximately 80% confluence. Cells were incubated with the noted concentrations of NADH, NRH or NMN and harvested with trypsin digestion. Unless otherwise specified, the treatment time of NADH or NRH was 3 h. The number of cells was counted by hemocytometer and trypan blue. The harvested cells were then pelleted at 3000×g for 3 min. After eliminating the residual medium, the cells were lysed with 7% perchloric acid to preserve NAD+, and then neutralized with NaOH (2 M) and $K_2HPO_4$ (500 mM). The determination of intracellular NAD+ concentrations was consistent with the assay, published in Li W, Sauve A A, "NAD(+) content and its role in mitochondria," *Methods Mol Biol* 2015, 1241:39-48, the entire content of which is incorporated herein by reference.

FIG. 1 is a graph of the NAD+ concentration changes in the assayed cells, with brown representing NADH, red representing NRH, purple representing NMN, and blue representing the vehicle control. The cellular NAD+ changes are indicated as fold over the control group, and data are expressed as mean±SD (n=3). *$p<0.01$ vs control; #$p<0.01$ vs NADH. As can be seen in FIG. 1, in cells exposed to NADH and NRH, the change in NAD+ concentrations were 2.7-11 times, which is much higher than the level of any other reported NAD+ precursor. FIG. 1 also shows that the effect of NADH on promoting intracellular NAD+ is greater than that of NRH. FIG. 1 also shows that in all cell lines, the NADH and NRH induced NAD+ levels were much higher than those induced by NMN. These data indicate that NADH and NRH are significantly (and surprisingly) more effective in stimulating NAD+ increases in cultured mammalian cells, and that NADH is more effective than NRH at the same task.

Figure 2A:
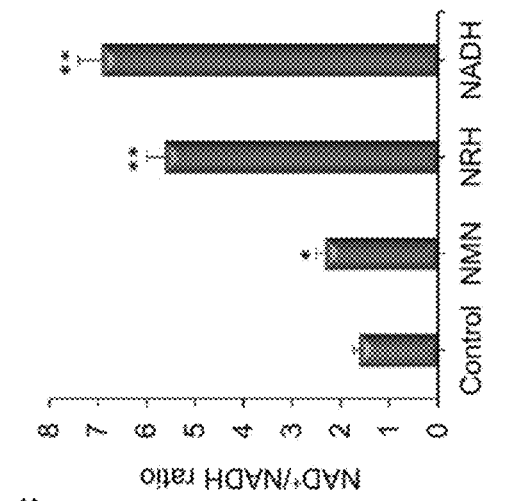
FIG. 2A is a graph of the dose-response of NADH in AML12 cells treated with 50, 100, 250, 500, 750, and 1000 µM NADH for 3 h.

A dose-response curve was also determined for hepatocyte AML12 cells. These cells were treated with rising concentrations of NADH for 3 h. FIG. 2A is a graph of this dose-response curve for NADH, and data are expressed as mean±SD. (n=3). *, $p<0.01$; **, $p<0.001$ vs Control. As shown in FIG. 2A, at the lowest NADH concentration, 50 µM, the concentration of NAD+ was approximately 4 times that of the corresponding control group. FIG. 2A also shows that saturation was achieved at 500 µM, with the concentration reaching 10 times that of the untreated control group.

Figure 2B:
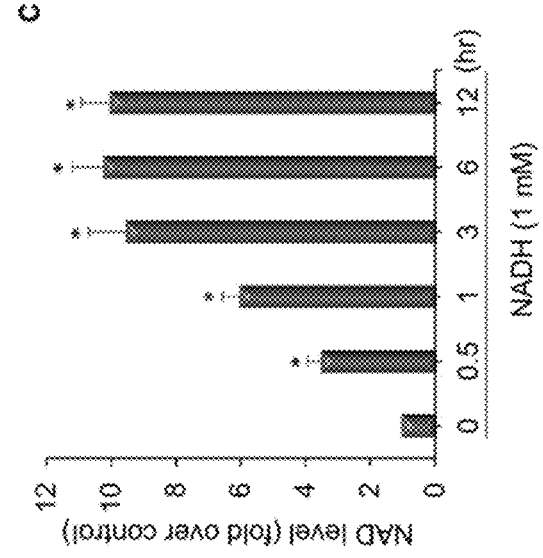
FIG. 2B is a graph of the NADH enhanced NAD+ levels in a time-dependent manner in AML12 cells incubated with 1 mM NADH for 0.5, 1, 3, 6, and 12 h.

Time course studies for NADH action were also carried out. AML12 cells were incubated with NADH for various incubation times (0-12 hr) and then harvested, and the NAD+ levels were assessed. FIG. 2B is a graph of these results, and data are expressed as mean±SD. (n=3). *, p<0.01; **, p<0.001 vs Control. As shown in FIG. 2B, the NAD+ concentration-increasing effects appeared as early as 0.5 hours, while full effects were present after 3 hours. Notably, after 12 hours of NADH treatment, NAD+ remained at a high concentration.

Figure 2C:
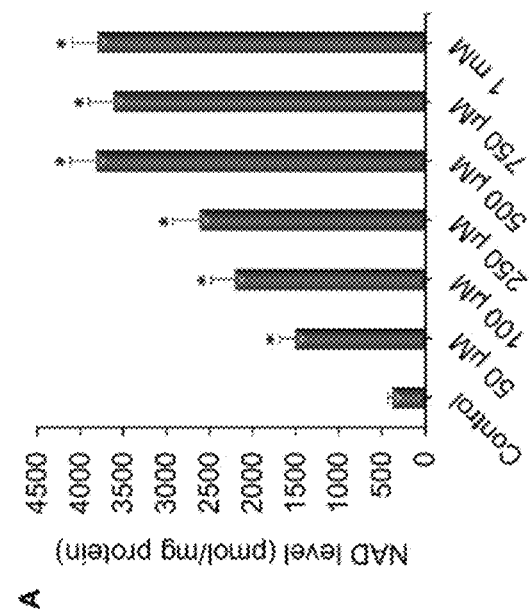
FIG. 2C is a graph of the $NAD^+$/NADH ratios measured in AML12 cells treated with 1 mM NMN, NRH or NADH for 6 h.

Finally, NAD$^+$/NADH ratios were measured in AML12 cells treated with 1 mM NMN, 1 mM NRH or 1 mM NADH for 6 h. FIG. 2C is a graph of these results, and data are expressed as mean±SD. (n=3). *, p<0.01; **, p<0.001 vs Control. As shown in FIG. 2C, NMN, NRH and NADH can significantly increase the NAD$^+$/NADH ratio of liver cells, but the effect of NRH and NADH is far superior to that of NMN.

Low Toxicity and Rescue Function in Genotoxicity

The sharp increase of NAD+ concentration indicates a possible toxicity to cells. To assess this toxicity, C2C12, Neuro2a and AML12 cells were treated with 1 mM NADH for 24 hours, and then the total cell numbers were measured. Specifically, C2C12, Neuro2a and AML12 cells were incubated with 1 mM NADH or NRH for 24 hours, and then detached by trypsin for cell counting. The cells were stained with trypan blue and then counted with a hemocytometer. In order to detect the apoptosis of AML12 cells, PBS, 1 mM NADH or NRH were added to 6 well plates and treated for 24 hours. The Annexin V/PI staining kit and Caspases3/7/ SYTOX dead cell staining kit (Life Technologies) were used and cells were counted with a BD FACSCelesta™ flow cytometer. The quadrants of apoptotic cells, necrotic cells and living cells were identified and quantified according to the manufacturer's instructions.

Figure 3A:
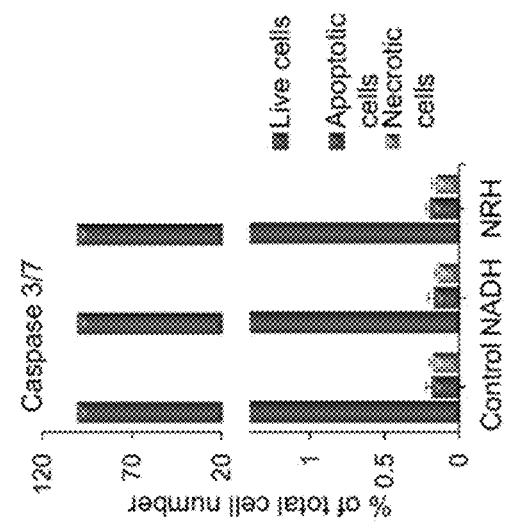
FIG. 3A is a graph of the total number of measured cells after treatment of C2C12, Neuro2a and AML12 cells with 1 mM NADH for 24 hours (brown) compared to a control (blue)
Figure 3B:
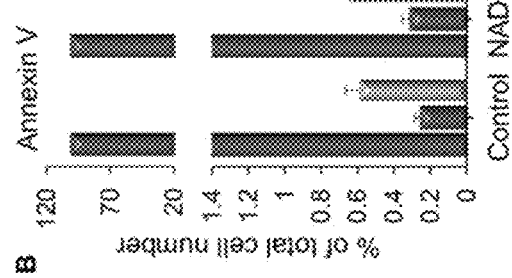
FIG. 3B is a graph of the total number of live (brown), apoptotic (blue) and necrotic (gray) AML12 cells stained for Annexin V and treated with 1 mM NADH or NRH compared to a control.
Figure 3C:
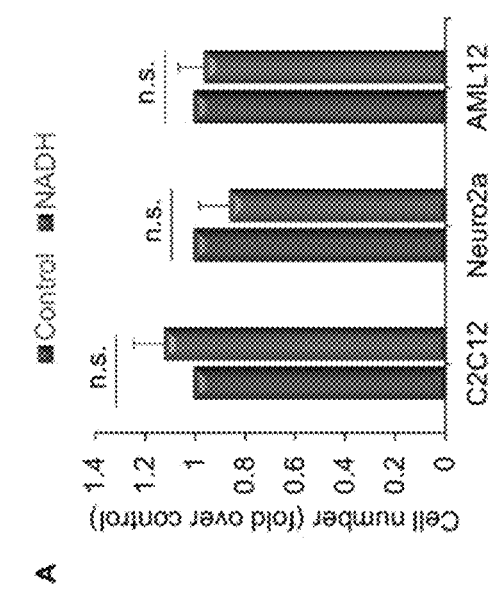
FIG. 3C is a graph of the total number of live (brown), apoptotic (blue) and necrotic (gray) AML12 cells stained for Caspase 3/7 and treated with 1 mM NADH or NRH compared to a control.

FIG. 3A is a graph of these results, showing NADH in brown and the control in blue, and data are expressed as mean±SD, n=4. To examine apoptotic markers, AML12 cells were stained for Annexin V and Caspase 3/7, and cells were counted with a flow cytometer. FIG. 3B shows the Annexin V results, and FIG. 3C shows the Caspase 3/7 results, both graphs showing live cells in brown, apoptotic cells in blue, and necrotic cells in gray. Data are expressed as mean±SD, n=3. Quadrants with live cells (brown), necrotic cells (gray) and apoptotic cells (blue) were quantified.

As shown in FIG. 3A, no obvious loss of cultured cells after exposure to 1 mM NADH for 24 hours was observed. For instance, the cell counts of C2C12, Neuro2a and AML12 cells were similar in the control group and in the NADH treated cells. Trypan blue positive cells were similar in these three cases, less than 5%, and there was no noteworthy difference in apoptosis markers. As shown in FIGS. 3B and 3C, compared with the control group, the Annexin V or caspase 3/7 groups had no significant changes in NADH and NRH treated cells. The results indicate that the cells were well tolerant to NADH and NRH in millimolar concentrations, and the high NAD+ level was also well tolerant, which would not produce obvious toxic effects at least within 24 hours.

Figure 4B:
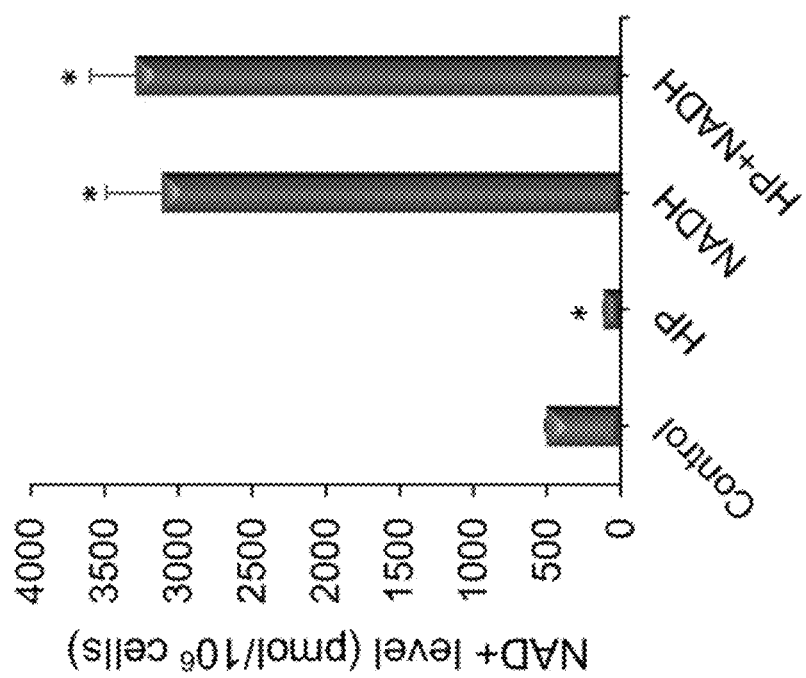
FIG. 4B is a graph comparing the NAD+ levels of AML12 cells treated with 500 µM HP in the presence or absence of 1 mM NADH for 3 h relative to a control.
Figure 4A:
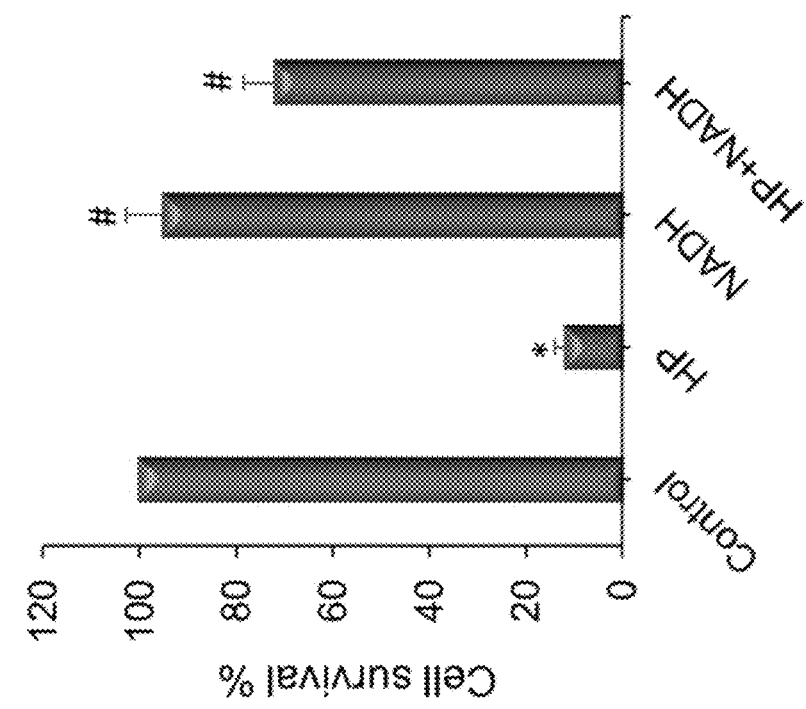
FIG. 4A is a graph comparing the cell survival rate of AML12 cells treated with 500 µM HP in the presence or absence of 1 mM NADH for 3 h relative to a control.

Because the increasing extent of NAD+ concentration is of interest, whether NADH can improve the cell survival rate under the stressful conditions of depletion of NAD+ was also assessed. To that end, as genotoxicity can lead to DNA damage, activate poly(ADP-ribose) polymerases and induce NAD+ depletion, genotoxicity was tested. Strong genotoxicity will lead to severe consumption of NAD+ by cells, resulting in cell death. To test genotoxicity, AML12 cells were treated with 500 μM hydrogen peroxide (HP) for 3 hours in the presence or absence of 1 mM NADH, and then the cells were counted and NAD+ was detected in the samples co-treated with NADH (1 mM) or its vehicle. FIG. 4A is a graph comparing the cell survival rate of the HP treated cells, NADH treated cells, and the HP+NADH treated cells relative to a control. And FIG. 4B is a graph comparing the NAD+ level of the HP treated cells, NADH treated cells, and the HP+NADH treated cells relative to a control. The cell survival rates and cellular NAD+ levels in FIGS. 4A-B are expressed as mean±SD. (n=3). *, p<0.01 vs control; #, p<0.01 vs HP.

As shown in FIG. 4A, under HP+NADH treatment, the cell survival rate increased from 12% to nearly 72%. Furthermore, as shown in FIG. 4B, in the HP+NADH treated cells, the NAD+ level remained high, while in HP cells, the NAD+ concentration was much lower than the control value. Similar results were achieved in INS1 cells, which contain insulin and are sensitive to HP (data not shown).

Figure 4D:
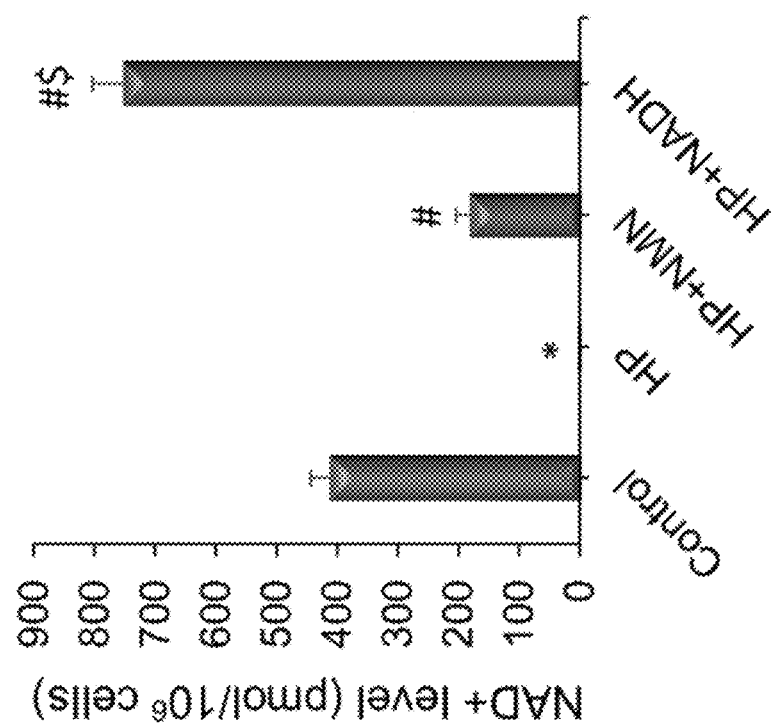
FIG. 4D is a graph comparing the NAD+ levels of the AML12 cells treated with 500 µM HP in the presence or absence of 250 µM NADH or 250 µM NMN for 3 h relative to a control.
Figure 4C:
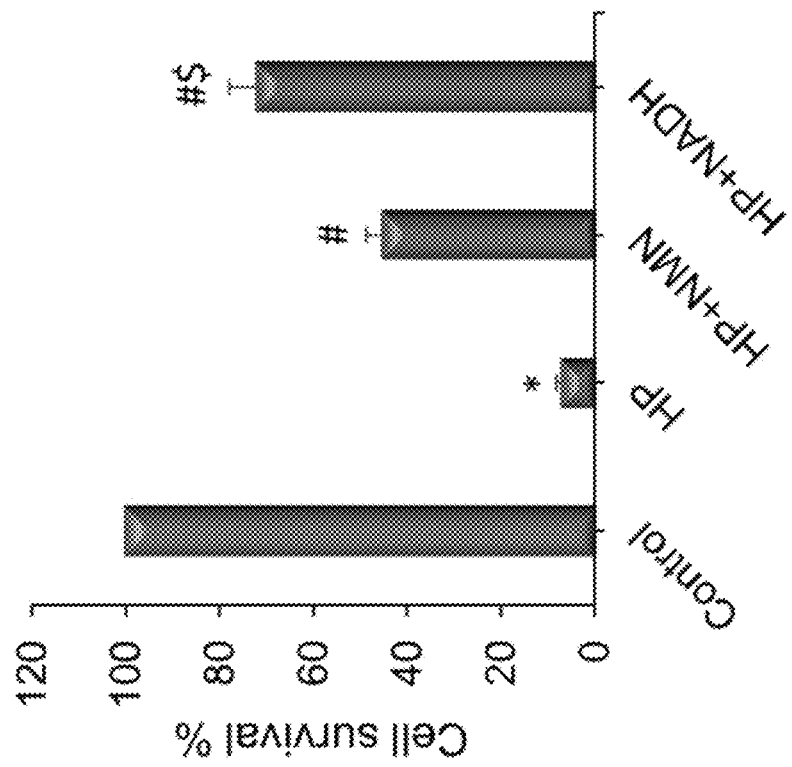
FIG. 4C is a graph comparing the cell survival rate of AML12 cells treated with 500 µM HP in the presence or absence of 250 µM NADH or 250 µM NMN for 3 h relative to a control.

The effects of NADH and NMN at a lower concentration (250 μM) on AML12 cells was also tested in a separate assay. Specifically, AML12 cells were treated with 500 μM HP in the presence or absence of 250 μm NADH or NMN for 3 h. FIG. 4C is a graph comparing the cell survival rate of the HP treated cells, HP+NADH treated cells, and the HP+NMN treated cells relative to a control. And FIG. 4D is a graph comparing the NAD+ level of the HP treated cells, HP+NADH treated cells, and the HP+NMN treated cells relative to a control. The cell survival rate and cellular NAD+ levels in FIGS. 4C-D are expressed as mean±SD. (n=3). *, p<0.01 vs control; #, p<0.01 vs HP; $, p<0.01 vs HP+NMN.

As can be seen in FIGS. 4C and 4D, NADH not only had a protective effect on NAD+ levels, but also had a protective effect on cell survival. Also, although FIGS. 4C and 4D show that NMN treatment is also effective, these graphs show that the effect of NMN on preserving NAD+ content and cell viability was much worse than that of NADH.

NADH In Vivo

In the below in vivo assays, C57BL/6J male mice (The Jackson Laboratory) (40 days of age) were used. They were kept under standard laboratory conditions with a temperature of 22±1° C., dark/light cycles of 12/12 h, and relative humidity of 55±5%. All animals had free access to food and water, except for indicated fasting periods (and where not indicated for fasting periods of 2 hours before administration).

To evaluate the biological effect of NADH on mice, 1000 mg/kg NADH was injected intraperitoneally into C57BL/6J mice, and the content of NAD+ in tissues was determined after 4 hours. Specifically, ten 8-week-old male C57BL/6J mice (The Jackson Laboratory) were kept in polycarbonate cages under a 12-h light/dark cycle with free access to food and water. Then, the mice were randomly divided into two groups: the treatment group was intraperitoneally injected with 1000 mg/kg NADH or NRH dissolved in PBS; and the control group was only injected with PBS (vehicle). Four hours later, the blood samples were collected by cardiac puncture and the mice were executed. Liver, brain, muscle, and adipose tissues were collected, instantly frozen in liquid nitrogen, and then stored at −80° C. until performance of the NAD+ analyses. In order to compare the effects of NADH or NRH and NMN at small doses, similar experiments were also conducted (i.e., intraperitoneal injection of 250 mg/kg NRH, 250 mg/kg NADH or 250 mg/kg NMN or PBS). Four hours later, the mice were killed and tissue samples were collected. All animal studies were performed according to the Guidelines for the Care and Use of Experimental Animals. For this NAD+ assay, about 100 mg of frozen tissue was crushed in liquid nitrogen and ultrasonically homogenized in 7% perchloric acid, and then the solution was neutralized and subjected to the NAD+ determination described here.

Figure 5B:
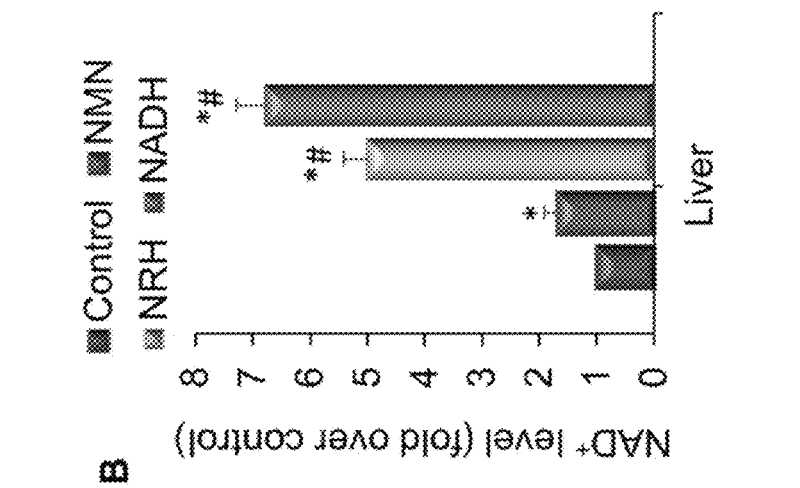
FIG. 5B is a graph comparing content of NAD+ in the liver of male C57BL/6J mice four hours after intraperitoneal injection of 250 mg/kg NMN (brown), 250 mg/kg NRH (green), 250 mg/kg NADH (purple) or vehicle alone (control, blue)
Figure 5A:
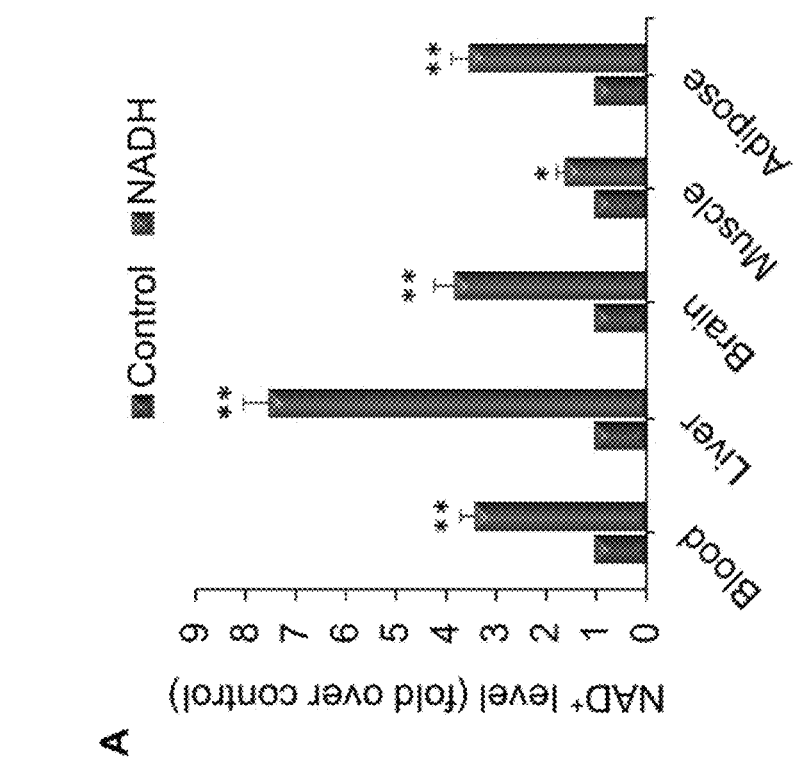
FIG. 5A is a graph comparing the content of NAD+ in the blood, liver, brain and epididymal adipose tissue of male C57BL/6J mice four hours after intraperitoneal injection of 1000 mg/kg NADH (brown) relative to a control (blue)

FIG. 5A is a graph comparing the NAD+ levels in blood, brain, liver, muscle and adipose after injection of NADH (brown) relative to a control (blue), and data are indicated as mean±SD. (n=4); *, p<0.05; **, p<0.01 vs their corresponding controls. As shown in FIG. 5A, the content of NAD+ in blood, brain and fat increased several times, with the highest increase in liver being more than 7 times within 4 hours. While the $NAD^+$-promoting effect of NADH appears to be the lowest in skeletal muscle, the results show that NADH is a potent NAD+ concentration enhancer. Indeed, after a single administration, the NAD+ concentration in many animal tissues and organs increased to varying and often significant degrees.

To evaluate whether NADH is more efficient than other NAD+ precursors in vivo, 250 mg/kg of NADH, NRH, NMN or vehicle alone was injected intraperitoneally, and the content of NAD+ in the liver was assessed 4 hours later. The results are shown in FIG. 5B, which is a graph comparing the NAD+ level (reported as fold over the control) in the liver after injection of the NADH (purple), NRH (green), NMN (brown) relative to the control (blue). Data are indicated as mean±SD. (n=4); *, p<0.05 vs their corresponding controls; #, p<0.05 vs NMN. As shown in FIG. 5B, in the liver, NADH increased the concentration of NAD+ by 680%, while NRH and NMN reached 500% and 170%, respectively. As can be seen from these results, at the same dose, NADH provides a surprisingly and significantly greater increase in NAD+ than NRH and NMN, and in the liver, NADH achieves a very significant increase in NAD+ even at low doses. This is consistent with the improvements in pharmacological efficacy observed by NADH (and NRH) as compared with other NAD+ precursors, and these findings further verify the results observed in the cell culture studies discussed above.

Effect of NADH and NRH on Blood Ethanol and Acetaldehyde Levels and Liver $NAD^+$/NADH Ratio In Vivo To assess the effect of NADH and NRH on blood ethanol and acetaldehyde levels, male C57BL/6J mice (6-8 mice) were fasted for 12 h, and then intragastrically administered with 500 mg/kg NRH, 500 mg/kg NADH or vehicle (control) 15 min prior to administration of 8 ml/kg ethanol (40% w/v, in tap water). More specifically, the mice were randomly divided into a normal group (untreated group), a control group and a treatment group, with 8 mice in each group. The mice in treatment groups received 500 mg/kg NRH, or 500 mg/kg NADH intragastrically 15 min prior to one single dose of 8 ml/kg ethanol (40% w/v, in tap water). This is the most commonly used animal alcohol intake model to imitate human alcoholism, which is 5-6 g/kg body weight, equivalent to 0.75 L whisky (40% v/v) consumed by a 75 kg human body. The control group was given the same ethanol solution and corresponding distilled water, while the normal group was only given corresponding distilled water. At different time points of the experiment, the mice were anesthetized by intraperitoneal injection of 10% chloral hydrate (350 mg/kg body weight). Blood and liver tissues were extracted from each animal, and liver tissues were frozen immediately for the described bioanalyses.

Blood samples were collected from the infraorbital venous plexus at different time points after the ethanol administration. Specifically, eyeball blood samples (0.3 mL) were taken and put into an 8 mL headspace vial containing 1.2 mL 0.6 M perchloric acid, 0.5 mL trichloroacetic acid (10%) and 0.3 mL internal standard (160 mg/L tertiary butanol), and the concentrations of ethanol and acetaldehyde were determined with headspace gas chromatography. Ethanol and acetaldehyde were quantified by gas chromatography as described by Isse T, Matsuno K, Oyama T, Kitagawa K, Kawamoto T, "Aldehyde dehydrogenase 2 gene targeting mouse lacking enzyme activity shows high acetaldehyde level in blood, brain, and liver after ethanol gavages," Alcohol Clin Exp Res 2005, 29(11):1959-1964, and Lee H S, Isse T, Kawamoto T, Woo H S, Kim A K, Park J Y, Yang M, "Effects and action mechanisms of Korean pear (*Pyrus pyrifolia* cv. Shingo) on alcohol detoxification," *Phytother Res* 2012, 26(11):1753-1758, the entire contents of both of which are incorporated herein by reference.

Figure 6C:
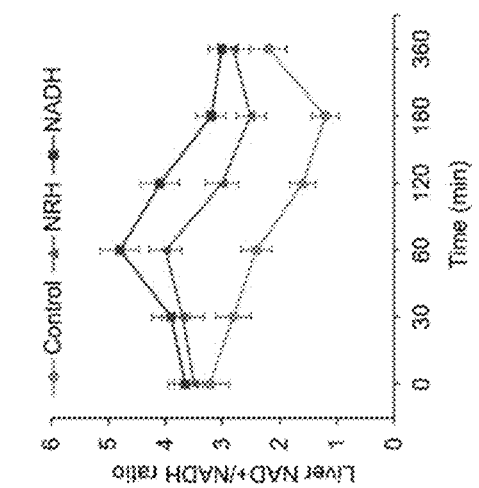
FIG. 6C is a graph comparing the liver redox fraction (i.e., NAD+/NADH ratio) vs. time (after ethanol administration) of mice administered with 500 mg/kg NRH (brown), 500 mg/kg NADH (red) or vehicle (control, blue) 15 min prior to administration of 8 ml/kg ethanol (40% w/v, in tap water)
Figure 6B:
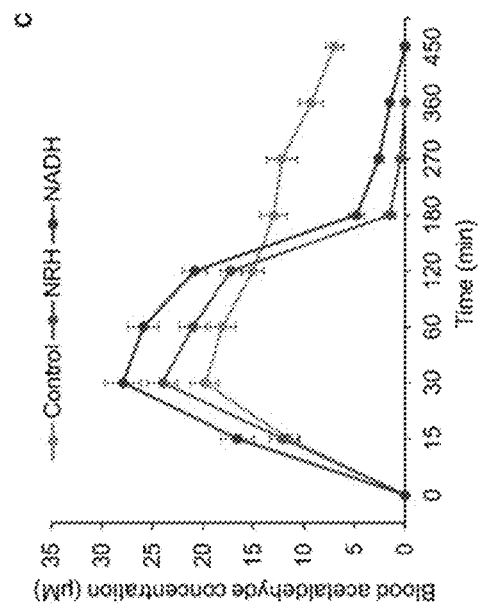
FIG. 6B is a graph comparing the blood acetaldehyde concentration vs. time (after ethanol administration) of mice administered with 500 mg/kg NRH (brown), 500 mg/kg NADH (red) or vehicle (control, blue) 15 min prior to administration of 8 ml/kg ethanol (40% w/v, in tap water)
Figure 6A:
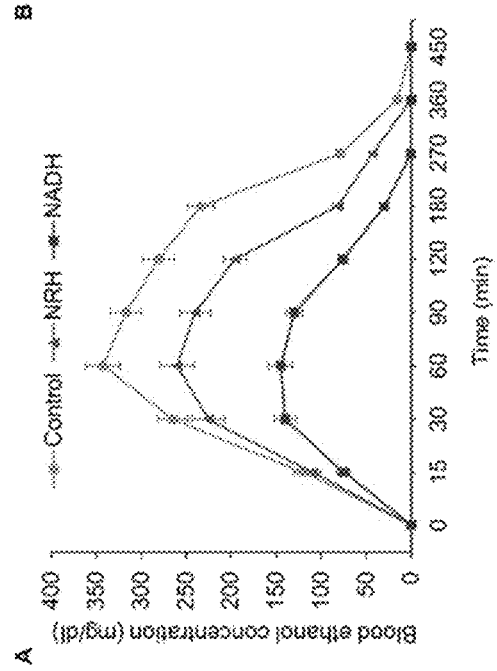
FIG. 6A is a graph comparing the blood alcohol (ethanol) concentration vs. time (after ethanol administration) of mice administered with 500 mg/kg NRH (brown), 500 mg/kg NADH (red) or vehicle (control, blue) 15 min prior to administration of 8 ml/kg ethanol (40% w/v, in tap water)

FIG. 6A is a graph comparing the blood ethanol concentration vs. time after the NRH administration (red) and NADH administration (brown) relative to the control (blue). And FIG. 6B is a graph comparing the blood acetaldehyde concentration vs. time after the NRH administration (red) and NADH administration (brown) relative to the control (blue). As shown in FIG. 6A, when NADH and NRH were administered orally 15 min before ethanol administration, the ethanol in the blood 30 minutes after ethanol administration was significantly reduced. Specifically, as shown in FIG. 6B, the rate of alcohol consumption in the first step of the alcohol metabolism process (i.e., conversion of alcohol to acetaldehyde) is markedly increased in mice administered with NADH (red) or NRH (brown) compared to the control (blue). Accordingly, this is shown in the more rapid decline in alcohol present in the blood over time, as shown in FIG. 6A. The results also show that NADH plays a faster and stronger role than NRH, starting to play a role just 15 minutes after ethanol administration.

Also, FIG. 6B shows that NADH and NRH treatments significantly increased the blood acetaldehyde levels in mice within two hours after ethanol administration, demonstrating that NADH and NRH can accelerate the first-pass speed of ethanol metabolism. Together with the data in FIG. 6A discussed above, this demonstrates that the administration of NADH or NRH prior to alcohol administration (or consumption) enables ethanol to be quickly metabolized to acetaldehyde, while acetaldehyde is slowly metabolized to acetic acid. Indeed, two hours after alcohol administration, the mice administered with NADH and NRH had significantly reduced acetaldehyde in the blood, and the effect of NRH was more significant than that of NADH. These results all indicate that NADH and NRH can accelerate alcohol metabolism.

In order to further clarify the anti-alcoholic function of NADH and NRH, the ratios of $NAD^+$/NADH in the liver of the mice treated as described above in connection with FIG. 6A was detected. Specifically, male C57BL/6J mice (6-8 mice) were fasted for 12 h, and then intragastrically administered with 500 mg/kg NRH, 500 mg/kg NADH or vehicle (control) 15 min prior to administration of 8 ml/kg ethanol (40% w/v, in tap water). The ratio of $NAD^+$/NADH in the liver was then measured at different times after ethanol administration.

The NAD+/NADH ratios were detected using a NAD+/NADH Quantification Colorimetric Kit (ABIN411692) in compliance with the manufacturer's instructions. Fresh tissue lysate was prepared from snap cryo-frozen liver samples stored in 80° C., and 20 mg liver was homogenized with $NAD^+$/NADH extraction buffer (400 µL). In order to quickly remove enzymes that may consume NADH, the samples were filtered through a 10 kD molecular weight cut-off filter before detection. To detect NADH, the extracted samples were heated to 60° C. in a heating block for 30 min to decompose NAD+. Concentrations were calculated using an NADH standard curve.

The results are shown in FIG. 6C, which is a graph comparing the liver NAD+/NADH ratio vs. time (after ethanol administration) of the NRH administration (red) and NADH administration (brown) relative to the control (blue). As shown in FIG. 6C, although the $NAD^+/NADH$ redox ratio in hepatocytes decreased as a consequence of ethanol metabolism, the administration of NADH or NRH significantly inhibited this decrease. This demonstrates that the administration of NADH or NRH to mice can modify the liver redox fraction, $NAD^+/NADH$, in a physiological manner, thus allowing the dehydrogenase reaction to work further towards the ethanol oxidation direction.

NADH and NRH Alleviate Acute Alcohol-Induced Hepatotoxicity

Liver marker enzymes in plasma, such as aspartate transaminase (AST) and alanine aminotransferase (ALT), are known as sensitive biochemical markers of early liver damage. Accordingly, the preventive and therapeutic effects of NADH and NRH on acute alcoholic liver injury were assessed by determining the levels of AST and ALT in the plasma after ethanol consumption. Specifically, to assess the preventive effects of NADH and NRH administration, male C57BL/6J mice were fasted for 12 h, and intragastrically administered with 500 mg/kg NRH, 500 mg/kg NADH or vehicle (as a control) 30 min prior to administration of 8 ml/kg ethanol (40% w/v, in tap water). Six hours after treatment with alcohol, blood samples were taken to detect biochemical indexes. To evaluate the therapeutic effects of NADH and NRH administrations, mice were given 40% ethanol every 24 h for 3 consecutive days, which caused acute liver injury. The control group was given the same amount of normal saline in place of the ethanol. After three days of alcohol treatment, the mice were treated with 500 mg/kg NADH or 500 mg/kg NRH every day for three consecutive days. The plasma levels of AST and ALT were measured for each of the mice in both assays, and the results are shown in FIGS. 7A and 7B.

The plasma levels of AST and ALT were determined by collecting blood samples in an anti-coagulant test tube and centrifuging at 1500 rpm for 10 minutes to attain plasma. The plasma AST and ALT activity was determined with a commercial kit (from Sigma-Aldrich) based on the manufacturer's instructions. FIG. 7A is a graph comparing the plasma level of AST in the mice exposed to alcohol alone (red), those exposed to NRH pre-treatment prior to alcohol exposure (left-most brown bar), those exposed to alcohol prior to NRH treatment (right-most brown bar), those pre-treated with NADH prior to alcohol exposure (left-most green bar), and those exposed to alcohol prior to treatment with NADH (right-most green bar) relative to the control (blue). And FIG. 7B is a graph comparing the plasma level of ALT in the mice exposed to alcohol alone (red), those exposed to NRH pre-treatment prior to alcohol exposure (left-most brown bar), those exposed to alcohol prior to NRH treatment (right-most brown bar), those pre-treated with NADH prior to alcohol exposure (left-most green bar), and those exposed to alcohol prior to treatment with NADH (right-most green bar) relative to the control (blue). The data are expressed as mean±SD (n=8); *p<0.01 vs control; #p<0.01 vs alcohol exposure.

Figure 7A:
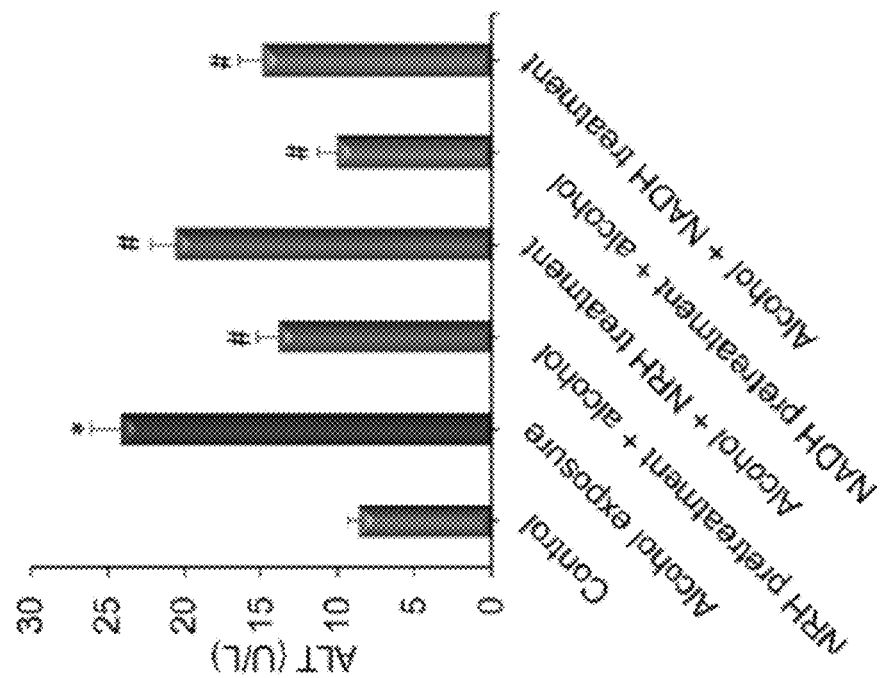
FIG. 7A is a graph comparing plasma levels of aspartate transaminase (AST) in male C57BL/6J mice intragastrically administered with 500 mg/kg NRH, 500 mg/kg NADH or vehicle (as a control) 30 min prior to administration of 8 ml/kg ethanol (40% w/v, in tap water)
Figure 7B:
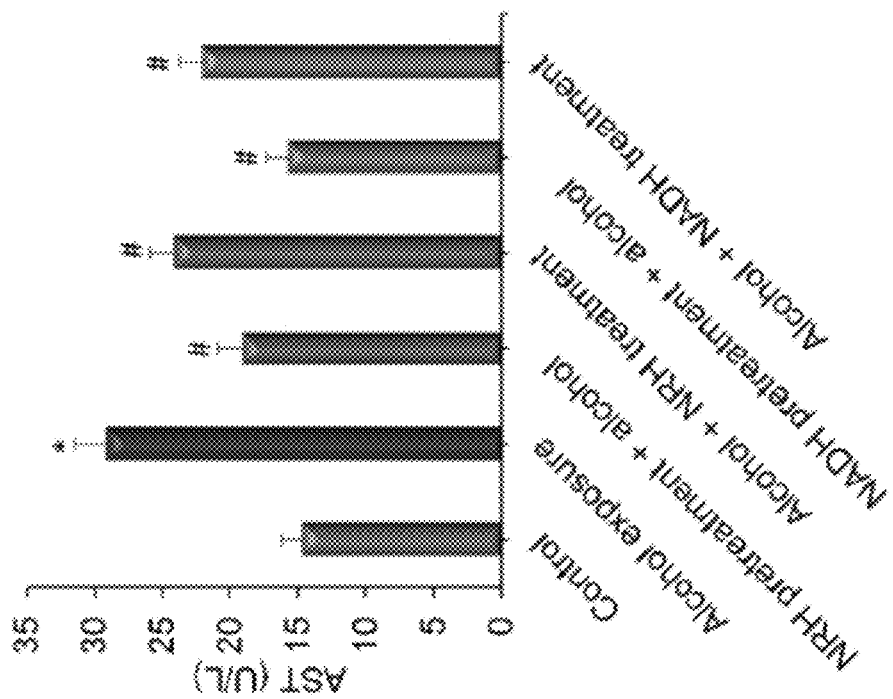
FIG. 7B is a graph comparing plasma levels of alanine aminotransferase (AST) in male C57BL/6J mice intragastrically administered with 500 mg/kg NRH, 500 mg/kg NADH or vehicle (as a control) 30 min prior to administration of 8 ml/kg ethanol (40% w/v, in tap water)

As shown in FIGS. 7A and 7B, acute alcohol exposure alone dramatically increased plasma AST and ALT levels. Compared with the control group, intake of NADH and NRH in the experimental group in advance of alcohol consumption may significantly reduce plasma AST and ALT levels, indicating that NADH and NRH may protect liver tissue against acute alcohol toxicity. In addition, FIGS. 7A and 7B also show that treatment with NADH or NRH after alcohol exposure can still significantly reduce AST and ALT levels, indicating that NADH and NRH have certain therapeutic effects on alcoholic hepatotoxicity, even if these effects are not as strong as the preventive effects.

Protective Effect of NADH and NRH Against the Oxidative Damage Caused by Acute Alcohol Ingestion (Pretreatment)

Oxidative stress plays a pathogenic role in many liver diseases such as hepatitis, NASH, fibrosis, liver cirrhosis and liver cancer. Therefore, monitoring endogenous/exogenous antioxidants and enzymes implicated in free radical control can make imperative contributions to the occurrence and development of the diseases, and also can be considered as a good adjuvant for anti-oxidant therapy.

To assess the protective effect of NADH and NRH on oxidative damage induced by acute alcohol intake in vivo, the biochemical parameters malondialdehyde (MDA) (an oxidative damage index) and superoxide dismutase (SOD) (an antioxidant indicator) in liver tissues were tested. Specifically, male C57BL/6J mice were fasted for 12 h, and intragastrically administered with 500 mg/kg NRH, 500 mg/kg NADH or vehicle (as a control) 15 min prior to administration of 8 ml/kg ethanol (40% w/v, in tap water). Six hours after treatment with alcohol, liver tissues were taken for determination of MDA and SOD.

Liver samples were prepared with homogenization in cold isotonic saline. The homogenate (10%, w/v) was centrifuged at 4500 g for 10 minutes and the supernatant was used for biochemical analysis. The MDA, SOD and TG levels were determined with commercial kits (Abcam, #ab118970; Thermofisher, #EIASODC and Abcam, ab65336) according to the manufacturer's instructions. The results were normalized to the total protein determined by BCA Protein Assay Kit (Abcam, #ab102536) according to the manufacturer's instructions.

Figure 8A:
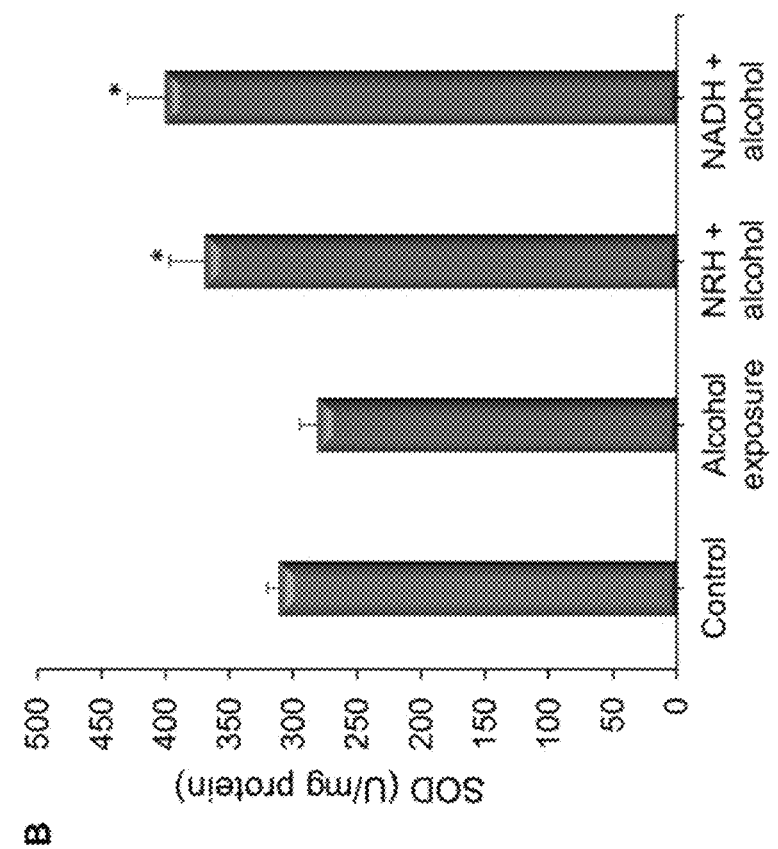
FIG. 8A is a graph comparing the malondiadehyde (MDA) activity of male C57BL/6J mice intragastrically administered with 500 mg/kg NRH, 500 mg/kg NADH or vehicle (as a control) 15 min prior to administration of 8 ml/kg ethanol (40% w/v, in tap water)

The results are shown in FIGS. 8A (MDA) and 8B (SOD), which are graphs comparing the MDA (FIG. 8A) or SOD (FIG. 8B) activity of the mice after alcohol exposure alone, after NRH pretreatment prior to alcohol exposure, and after NADH pretreatment prior to alcohol exposure relative to the control. The data in both FIGS. 8A and 8B are expressed as mean±SD (n=8), *p<0.01 vs control; #p<0.01 vs alcohol exposure.

Figure 8B:
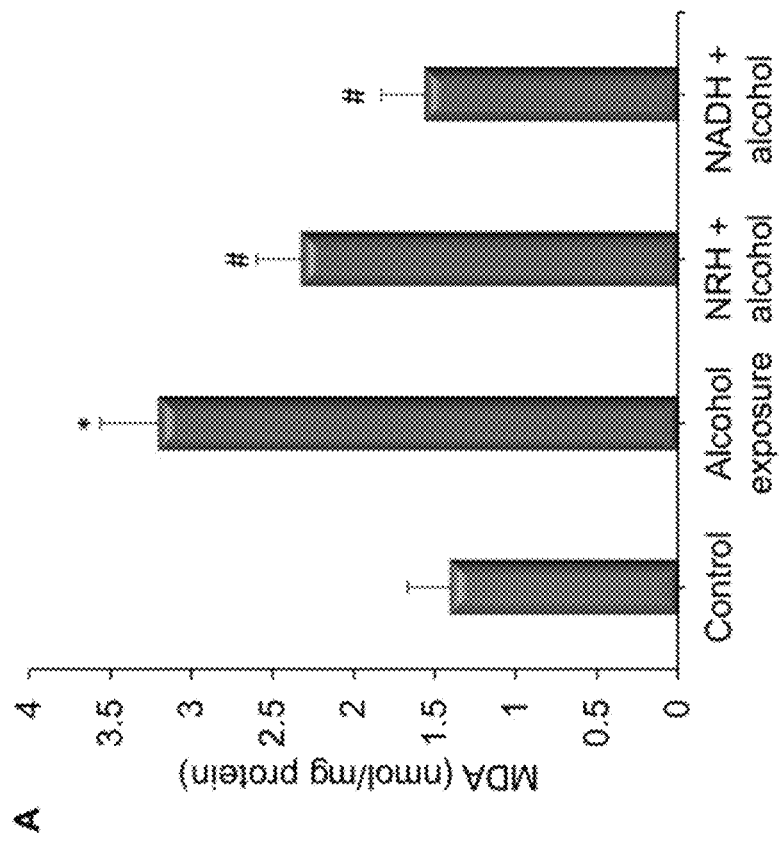
FIG. 8B is a graph comparing the superoxide dismutase (SOD) activity of male C57BL/6J mice intragastrically administered with 500 mg/kg NRH, 500 mg/kg NADH or vehicle (as a control) 15 min prior to administration of 8 ml/kg ethanol (40% w/v, in tap water)

As shown in FIGS. 8A and 8B, SOD activity in the experimental group decreased, and MDA content augmented dramatically, almost twice as much as that in the control group. These results show that administration of NADH and NRH in advance (i.e., prior to alcohol administration or consumption) can significantly reduce MDA content in the liver and increase SOD activity in alcohol-loaded mice. Together, these results indicate that NADH and NRH may protect the liver from high oxidative stress caused by acute alcohol intake.

Effect of NADH and NRH on Liver Histopathology and Lipid Metabolism

By assessing the histological characteristics of liver tissues in different groups of mice, the alcoholic liver injury and the hepatoprotective effects of NADH and NRH were further studied. For this assay, male C57BL/6J mice were fasted for 12 h, and intragastrically administered with 500 mg/kg NRH, 500 mg/kg NADH or vehicle 15 min prior to administration of 8 ml/kg ethanol ingestion (40% w/v, in tap water). Liver histopathology was detected by Oil Red 0 staining. According to the standard operating procedure, some liver tissues were fixed for histopathological assessment. The other part of the liver was stored at −80° C. 10 mm thick frozen sections were stained with Oil Red 0 to detect liver steatosis. The stained sections were examined by a 400× optical microscope. The level of VLDL in serum samples was examined with a Bio-Tek synergy2 Multiscan Spectrum (Botten Instruments Co.).

Figure 9A:
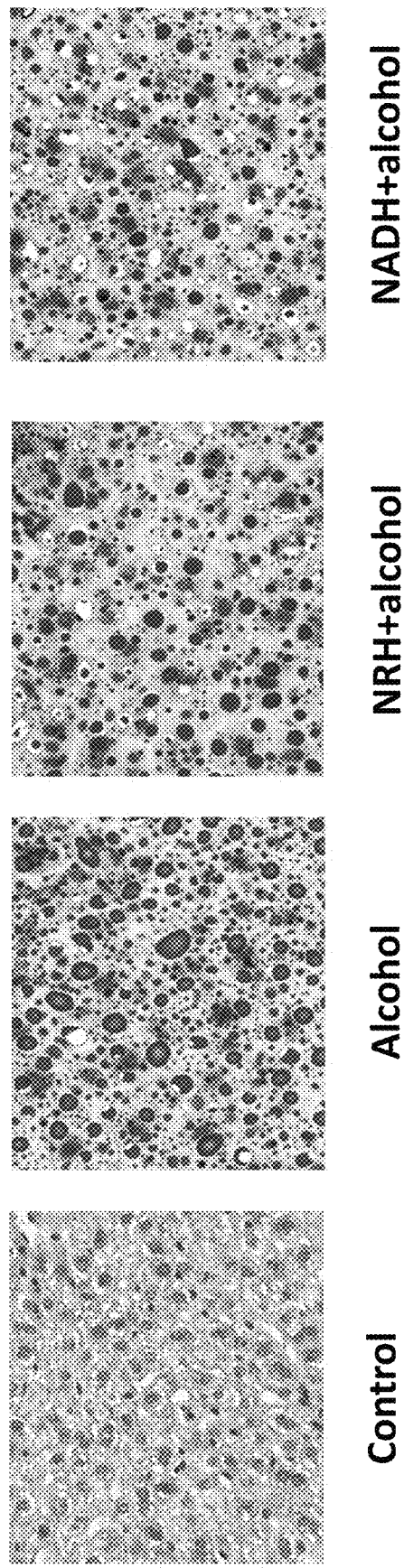
FIG. 9A depicts light microscope (magnification 400×) photographs of Oil Red 0 stained liver specimens of male C57BL/6J control mice, male C57BL/6J mice after administration of 8 ml/kg ethanol (40% w/v, in tap water) alone, male C57BL/6J mice after pre-treatment with 500 mg/kg NRH 15 min prior to administration of 8 ml/kg ethanol (40% w/v, in tap water), and male C57BL/6J mice after pre-treatment with 500 mg/kg NADH prior to administration of 8 ml/kg ethanol (40% w/v, in tap water)

The microscope photographs of the control mice, the mice after alcohol exposure alone, the mice after pre-treatment with NRH prior to alcohol exposure, and the mice after pre-treatment with NADH prior to alcohol exposure are shown in FIG. 9A. As can be seen in FIG. 9A, Oil Red O staining showed that the structure of the liver tissue in the control group was normal, and there was no collagen deposition and extracellular matrix (ECM) deposition in the liver tissue. However, the liver fatty degeneration of the mice in the ethanol group (i.e., alcohol exposure alone) was very apparent. FIG. 9A also shows that the groups pretreated with NADH and NRH had noticeably decreased degrees of fatty degeneration, demonstrating the protective effects of NADH and NRH.

To evaluate alcoholic liver injury, the index of liver lipid metabolism (i.e., the triglyceride (TG) level in liver tissue) and the activity of serum Very Low Density Lipoprotein (VLDL) were also measured in the mice treated as described above in connection with FIG. 9A. These results are shown in FIG. 9B (liver triglycerides) and 9C (VLDL), which are graphs comparing the triglyceride (TG) levels (FIG. 9B) and VLDL levels (FIG. 9C) of the mice after alcohol exposure alone, the mice after pre-treatment with NRH prior to alcohol exposure, and the mice after pre-treatment with NADH prior to alcohol exposure relative to the control. The data in both FIGS. 9A and 9B are expressed as mean±SD (n=8); *$p<0.01$ vs control; #$p<0.01$ vs alcohol exposure.

Figure 9C:
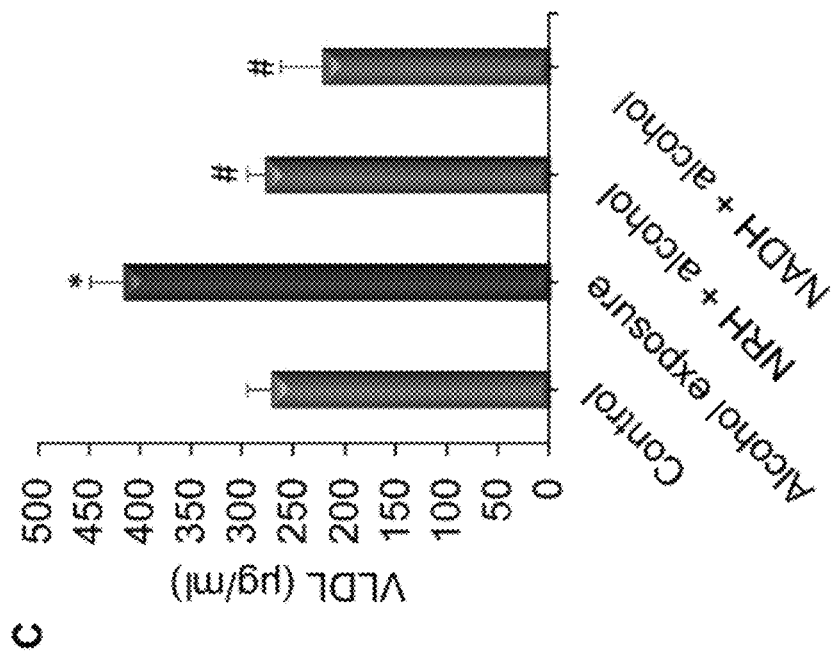
FIG. 9C is a graph comparing the activity of serum Very Low Density Lipoprotein (VLDL) of male C57BL/6J mice after administration of 8 ml/kg ethanol (40% w/v, in tap water) alone, male C57BL/6J mice after pre-treatment with 500 mg/kg NRH 15 min prior to administration of 8 ml/kg ethanol (40% w/v, in tap water), and male C57BL/6J mice after pre-treatment with 500 mg/kg NADH prior to administration of 8 ml/kg ethanol (40% w/v, in tap water) relative to the control.
Figure 9B:
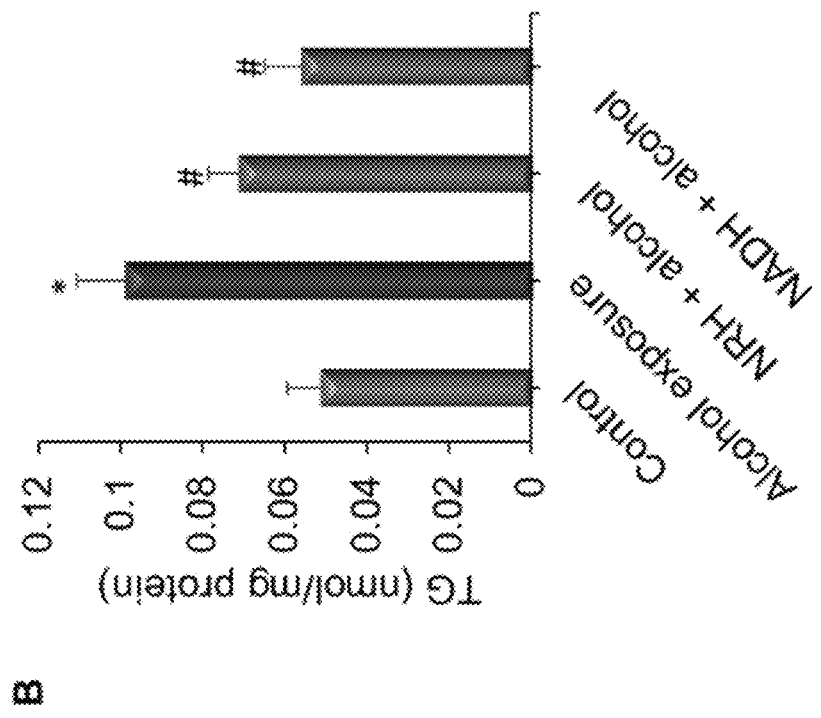
FIG. 9B is a graph comparing the triglyceride (TG) levels of male C57BL/6J mice after administration of 8 ml/kg ethanol (40% w/v, in tap water) alone, male C57BL/6J mice after pre-treatment with 500 mg/kg NRH 15 min prior to administration of 8 ml/kg ethanol (40% w/v, in tap water), and male C57BL/6J mice after pre-treatment with 500 mg/kg NADH prior to administration of 8 ml/kg ethanol (40% w/v, in tap water) relative to the control.

As shown in FIGS. 9B and 9C, compared with the normal control group, liver TG and serum VLDL activities of mice exposed to alcohol alone increased by 1.9 times and 1.5 times, respectively. Compared with the model control group (i.e., alcohol exposure alone), the mice pretreated with NADH and NRH prior to alcohol exposure had decreased liver index, TG and VLDL levels, suggesting that NADH and NRH can alleviate the abnormal lipid metabolism in acute alcoholic liver damage.

Effect of NADH and NRH on Tolerance to Acute Alcohol Exposure

Alcohol acts on the central nervous system, causing various behavioral and/or cognitive problems, e.g., loss of righting reflex (LORR). The tolerance of mice to the hypnotic effect induced by alcohol can be assessed by the loss of righting reflex (LORR) test, as discussed in Ozburn A R, Harris R A, Blednov Y A, "Chronic voluntary alcohol consumption results in tolerance to sedative/hypnotic and hypothermic effects of alcohol in hybrid mice," *Pharmacol Biochem Behav* 2013, 104:33-39, the entire content of which is incorporated herein by reference. LORR is defined as the phenomenon that mice cannot correct themselves three times within 30 seconds after alcohol intake. LORR latency is defined as the time from drinking to occurrence of LORR, and LORR duration is defined as the time from occurrence to recovery of LORR.

Figure 10A:
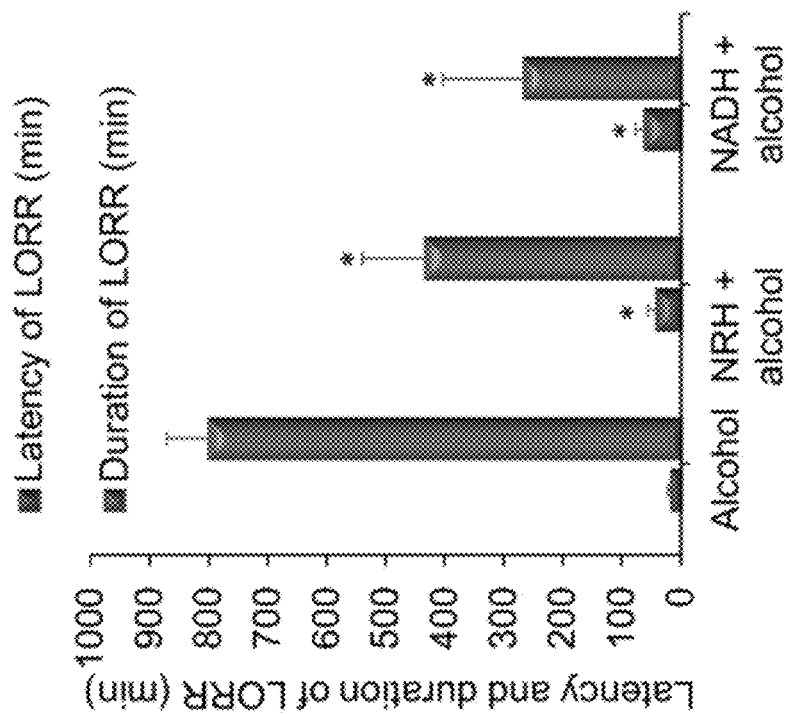
FIG. 10A is a graph comparing the LORR rate of male C57BL/6J mice after pre-treatment with 500 mg/kg NRH 15 min prior to administration of 8 ml/kg ethanol (40% w/v, in tap water), and male C57BL/6J mice after pre-treatment with 500 mg/kg NADH prior to administration of 8 ml/kg ethanol (40% w/v, in tap water) relative to male C57BL/6J mice after administration of 8 ml/kg ethanol (40% w/v, in tap water) alone.
Figure 10B:
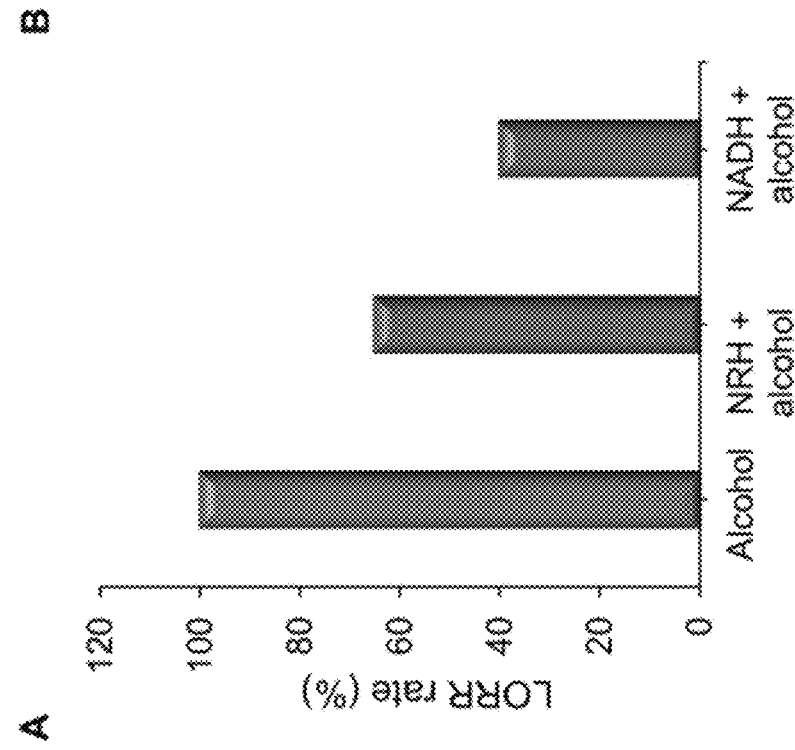
FIG. 10B a graph comparing the LORR latency of male C57BL/6J mice after pre-treatment with 500 mg/kg NRH 15 min prior to administration of 8 ml/kg ethanol (40% w/v, in tap water), and male C57BL/6J mice after pre-treatment with 500 mg/kg NADH prior to administration of 8 ml/kg ethanol (40% w/v, in tap water) relative to male C57BL/6J mice after administration of 8 ml/kg ethanol (40% w/v, in tap water) alone.

To assess the effect of NADH and NRH treatment on the effects of alcohol on the central nervous system, male C57BL/6J mice were fasted for 12 h, and intragastrically administered with 500 mg/kg NRH, 500 mg/kg NADH or vehicle 15 min prior to administration of 8 ml/kg ethanol ingestion (40% w/v, in tap water). Fisher's exact probability test was used to analyze the loss of righting reflex (LORR) in the mice. The results are shown in FIGS. 10A and 10B, which are graphs comparing the LORR rate (FIG. 10A) and LORR latency (FIG. 10B) of the mice pretreated with NRH prior to alcohol exposure and the mice pretreated with NADH prior to alcohol exposure relative to the model control mice (exposed to alcohol alone). The data representing LORR latency and duration are expressed as mean±SD (n=10); *$p<0.05$ vs alcohol group.

As shown in FIGS. 10A and 10B, in the model group (i.e., alcohol exposure alone), acute alcohol intake induced LORR (100% LORR rate) in all mice within an average time of 14.76 minutes (latency), and the average length of the LORR was about 798.68 minutes. However, the mice pretreated with NADH and NRH exhibited a decrease in the LORR rate and duration as well as prolonged latency. Notably, less than half of the mice in the NADH pretreatment group had a righting reflex after drinking alcohol (i.e., more than half of the mice had a loss of righting reflex), and the LORR duration for those that did have an LORR was significantly shortened to 265.00 minutes, almost one third of that in the model group. Additionally, the average latency increased to 60.24 minutes, which was 4 times that of the model group. Accordingly, these data show that administration of NADH and NRH prior to alcohol exposure can dramatically improve the tolerance of mice to acute alcohol exposure.

As discussed above, treatment with NADH or NRH either before or after alcohol consumption can have a profound effect on various acute alcoholic liver damage. Indeed, as discussed in more detail above, NADH and NRH have protective/preventive effects when used as a pre-treatment prior to alcohol consumption, limiting the extent of acute alcoholic liver damage by, e.g., reducing the alcohol (i.e., ethanol) concentration in the blood and promoting faster metabolism of ethanol to acetaldehyde, reducing hepatotoxicity due to alcohol consumption, protecting the liver from high oxidative stress caused by acute alcohol intake, and decreasing liver index, TG and VLDL levels to alleviate the abnormal lipid metabolism in acute alcoholic liver damage. And NADH and NRH treatment also improves cognitive impairment associated with alcohol intake, as discussed above with respect to the significant reductions observed LORR onset, duration and latency. Additionally, as also discussed in more detail above, NADH and NRH administered after alcohol consumption can reduce AST and ALT levels, thereby reducing alcoholic hepatotoxicity even after alcohol consumption.

While certain exemplary embodiments of the present disclosure have been illustrated and described, those of ordinary skill in the art will recognize that various changes and modifications can be made to the described embodiments without departing from the spirit and scope of the present invention, and equivalents thereof, as defined in the claims that follow this description. For example, although certain components may have been described in the singular, i.e., "a" compound, "an" excipient, and the like, one or more of these components in any combination can be used according to the present disclosure.

Also, although certain embodiments have been described as "comprising" or "including" the specified components, embodiments "consisting essentially of" or "consisting of" the listed components are also within the scope of this disclosure. For example, while embodiments of the present disclosure are described as comprising a dietary supplement or pharmaceutical composition comprising an exogenous source of NAD+ and a pharmaceutically acceptable carrier, embodiments consisting essentially of or consisting of these components are also within the scope of this disclosure. Accordingly, a dietary supplement or pharmaceutical composition may consist essentially of an exogenous source of NAD+ and a pharmaceutically acceptable carrier. In this context, "consisting essentially of" means that any additional components will not materially affect the chemical, physical, therapeutic, preventive, dietary or pharmaceutical properties of the dietary supplement or pharmaceutical composition.

As used herein, unless otherwise expressly specified, all numbers such as those expressing values, ranges, amounts or percentages may be read as if prefaced by the word "about," even if the term does not expressly appear. Further, the word "about" is used as a term of approximation, and not as a term of degree, and reflects the penumbra of variation associated with measurement, significant figures, and interchangeability, all as understood by a person having ordinary skill in the art to which this disclosure pertains. Any numerical range recited herein is intended to include all sub-ranges subsumed therein. Plural encompasses singular and vice versa. For example, while the present disclosure may describe "a" compound or "an" excipient, a mixture of such materials can be used. When ranges are given, any endpoints of those ranges and/or numbers within those ranges can be combined within the scope of the present disclosure. The terms "including" and like terms mean "including but not limited to," unless specified to the contrary.

Notwithstanding that the numerical ranges and parameters set forth herein may be approximations, numerical values set forth in the Examples and Experiments are reported as precisely as is practical. Any numerical value, however, inherently contains certain errors necessarily resulting from the standard variation found in their respective testing measurements. The word "comprising" and variations thereof as used in this description and in the claims do not limit the disclosure to exclude any variants or additions.

What is claimed is:

1. A method of treating, ameliorating, or reducing the likelihood of developing acute alcoholic liver damage in a subject, the method comprising administering to the subject a composition comprising:
an effective amount of NADH (nicotinamide adenine dinucleotide (NAD)+hydrogen (H)) and/or NRH (dihydronicotinamide nucleoside).

2. The method of claim 1, wherein the administration of the composition comprises administering the composition prior to the subject consuming or being exposed to alcohol.

3. The method of claim 1, wherein the administration of the composition comprises administering the composition after the subject has consumed or been exposed to alcohol.

4. The method of claim 1, wherein the administration of the composition comprises orally administering to the subject a dietary supplement comprising the composition.

5. The method of claim 1, wherein the administration of the composition comprises orally administering to the subject a pharmaceutical composition comprising the composition.

6. The method of claim 5, wherein the pharmaceutical composition comprises one or more pharmaceutically acceptable carriers, excipients, adjuvants and/or diluents.

7. The method of claim 1, wherein the administration of the composition comprises administering a dose of the NADH and/or NRH of about 0.01 mg/kg to about 20 mg/kg per day.

8. The method of claim 4, wherein the administration of the composition comprises administering a daily dose of the NADH and/or NRH.

9. The method of claim 7, wherein the administration of the composition comprises administering a daily dose of the NADH and/or NRH for a period of 1 day to 14 days.

10. A method of increasing a subject's tolerance of alcohol, the method comprising administering to the subject a composition comprising:
an effective amount of NADH (nicotinamide adenine dinucleotide (NAD)+hydrogen (H)) and/or NRH (dihydronicotinamide nucleoside).

11. The method of claim 10, wherein the administration of the composition comprises administering the composition prior to the subject consuming or being exposed to alcohol.

12. The method of claim 10, wherein the administration of the composition comprises orally administering to the subject a dietary supplement comprising the composition.

13. The method of claim 10, wherein the administration of the composition comprises administering a dose of the NADH and/or NRH of about 0.01 mg/kg to about 20 mg/kg per day.

14. The method of claim 12, wherein the administration of the composition comprises administering a daily dose of the NADH and/or NRH.

15. A method of treating, alleviating, or reducing the severity of or the likelihood of developing the symptoms of an alcohol hangover in a subject, the method comprising administering to the subject a composition consisting comprising:
an effective amount of NADH (nicotinamide adenine dinucleotide (NAD)+hydrogen (H)) and/or NRH (dihydronicotinamide nucleoside).

16. The method of claim 15, wherein the administration of the composition comprises administering the composition prior to the subject consuming or being exposed to alcohol.

17. The method of claim 15, wherein the administration of the composition comprises administering the composition after the subject has consumed or been exposed to alcohol.

18. The method of claim 15, wherein the administration of the composition comprises orally administering to the subject a dietary supplement comprising the composition.

19. The method of claim 15, wherein the administration of the composition comprises administering a dose of the NADH and/or NRH of about 0.01 mg/kg to about 20 mg/kg per day.

* * * * *